United States Patent
Siedler et al.

(10) Patent No.: US 10,385,349 B2
(45) Date of Patent: Aug. 20, 2019

(54) SENSOR FOR NADP (H) AND DEVELOPMENT OF ALCOHOL DEHYDROGENASES

(71) Applicant: FORSCHUNGSZENTRUM JULICH GMBH, Julich (DE)

(72) Inventors: Solvej Siedler, Aachen (DE); Georg Schendzielorz, Dusseldorf (DE); Stephan Binder, Eschweiler (DE); Lothar Eggeling, Julich (DE); Stephanie Bringer-Meyer, Julich (DE); Michael Bott, Julich (DE)

(73) Assignee: Forschungszentrum Julich GmbH, Julich (DE)

( * ) Notice: Subject to any disclaimer, the term of this patent is extended or adjusted under 35 U.S.C. 154(b) by 489 days.

(21) Appl. No.: 14/424,559

(22) PCT Filed: Aug. 16, 2013

(86) PCT No.: PCT/EP2013/002481
§ 371 (c)(1),
(2) Date: Feb. 27, 2015

(87) PCT Pub. No.: WO2014/032777
PCT Pub. Date: Mar. 6, 2014

(65) Prior Publication Data
US 2015/0299715 A1 Oct. 22, 2015

(30) Foreign Application Priority Data
Aug. 28, 2012 (DE) .................. 10 2012 017 026

(51) Int. Cl.
*C12N 15/70* (2006.01)
*C12Q 1/6897* (2018.01)

(52) U.S. Cl.
CPC ........... *C12N 15/70* (2013.01); *C12Q 1/6897* (2013.01)

(58) Field of Classification Search
None
See application file for complete search history.

(56) References Cited

U.S. PATENT DOCUMENTS

2005/0067303 A1  3/2005  Wong et al.

FOREIGN PATENT DOCUMENTS

CN        1525163      9/2004
CN      101305280     11/2008
(Continued)

OTHER PUBLICATIONS

Mauri et al., Vascular Cell Adhesion Molecule-1 (VCAM-1) Gene Transcription and Expression Are Regulated through an Antioxidant-sensitive Mechanism in Human Vascular Endothelial Cells; J Clin. Invest. vol. 92, pp. 1866-1874, 1993.*
(Continued)

*Primary Examiner* — Addison D Ault
(74) *Attorney, Agent, or Firm* — Blank Rome LLP

(57) ABSTRACT

The present invention relates to an NADP(H) nanosensor comprising
i) a nucleic acid sequence to which a regulator is capable of binding, wherein the oxidation state of the regulator depends on the NADP(H) availability;
ii) a promoter sequence following the nucleic acid sequence i), to which an RNA polymerase is capable of binding, wherein the affinity of the RNA polymerase for the promoter sequence is influenced by the oxidation state of the regulator;
iii) a nucleic acid sequence which is under the control of the promoter sequence ii) and which codes for an autofluorescent protein.

(Continued)

The present invention also relates to a cell, a method for isolating genes which code for NADP(H)-dependent enzymes, and the use of an NADP(H) nanosensor.

6 Claims, 3 Drawing Sheets

Specification includes a Sequence Listing.

(56) References Cited

FOREIGN PATENT DOCUMENTS

| | | |
|---|---|---|
| CN | 101386828 | 3/2009 |
| CN | 102517378 | 6/2012 |
| JP | 2005-517960 | 6/2005 |

OTHER PUBLICATIONS

Krapp et al.; "The soxRS Response of *Escherichia coli* can be induced in the absence of oxidative stress and oxygen by modulation of NADPH content"; Microbiology; vol. 157; No. Part 4; Apr. 2011; pp. 957-965.

Lee Jin Hyung et al.; "An oxidative stress-specific bacterial cell array chip for toxicity analysis"; Biosensors and Bioelectronics; vol. 22; No. 9-10; Apr. 2007; pp. 2223-2229.

Kabir et al.; "Investigation into the effect of soxR and soxS genes deletion on the central metabolism of *Escherichia coli* based on gene expressions and enzyme activities"; Biochemical Engineering Journal; vol. 30; No. 1; May 1, 2006; pp. 39-47.

Kim Yang Hee et al.; "Iron oxide/carbon black ($Fe_2O_3$/CB) composite electrode for the detection of reduced nicotinamide cofactors using an amperometric method under a low overpotential"; Biosensors and Bioelectronics; vol. 25; No. 5; Jan. 2010; pp. 1160-1165.

Kobayashi Kazuo et al.; "Activation of SoxR-Dependent Transcription in Pseudomonas aeruginosa"; Journal of Biochemistry; vol. 136; No. 5; Nov. 2004; pp. 607-615.

Lu et al.; "Quantitative and Kinetic Study of Oxidative Stress Regulons Using Green Fluorescent Protein"; Wiley InterScience; Jan. 25, 2005; pp. 574-587.

D'Autreaux et al.; "ROS as signaling molecules: Mechanisms that generate specificity in ROS homeostasis"; Nature Reviews Molecular Cell Biology; vol. 8, Oct. 2007; pp. 813-824.

\* cited by examiner

SENSOR FOR NADP (H) AND DEVELOPMENT OF ALCOHOL DEHYDROGENASES

RELATED APPLICATION

This application is a National Stage application of PCT/EP2013/002481 filed Aug. 16, 2013, which claims priority to German Patent Application No. 10 2012 017 026.2 filed Aug. 28, 2012, the entire disclosures of which are hereby incorporated by reference.

The present invention relates to an NADP(H) nanosensor, a cell, a method for isolating genes which code for NADP(H)-dependent enzymes, and the use of an NADP(H) nanosensor.

The use of NADP(H)-dependent enzymes in the chemical industry as a catalyst is disclosed in a large number of examples. Thus, alcohol dehydrogenases, also called oxidoreductases or ketoreductases, are employed for reducing carbonyl groups. In particular, the enantiospecificity and regiospecificity is used for reducing prochiral ketones. Examples of such ketoreductases which serve for the synthesis of useful chemical compounds are the asymmetric reduction of 4-chloroacetoacetate esters (U.S. Pat. Nos. 5,559,030, 5,700,670 and 5,891,685), the reduction of dicarboxylic acids (U.S. Pat. No. 6,399,339), the reduction of tert-butyl-(S)-chloro-5-hydroxy-3-oxohexanoate (U.S. Pat. No. 6,645,746 and WO-A-01/40450), the reduction of pyrrolotriazine-based compounds (US-A-2006/0286646), the reduction of substituted acetophenones (U.S. Pat. No. 6,800,477, US-A-2012/0178142) or the reduction of hydroxythiolanes (WO-A-2005/054491), alpha-haloketones are likewise reduced enzymatically to alpha-haloalcohols. This can also be carried out by isolated enzymes or with whole cells (WO-A-2008/038050). By means of specific alcohol dehydrogenases from *Lactobacillus brevis* or *Thermoanaerobium brokii*, the reduction of the 8-chloro-6-oxooctanoic acid alkyl ester to the (R)- or (S)-8-chloro-6-hydroxyoctanoic acid alkyl ester, which is used as the precursor of (R)-α-lipoic acid and (S)-α-lipoic acid respectively, is effected (U.S. Pat. No. 7,157,253). Processes for the preparation of optically active alkanols wherein the preparation of, for example, (1S)-3-methylamino-1-(2-thienyl)-propan-1-ol und (1S)-3-chloro-1-(2-thienyl)-propan-1-ol is carried out by enzymatic reduction of the corresponding ketones are also described (WO-A-2006/094945). A process for preparing 3-hydroxybutyl 3-hydroxybutyrates enantiospecifically by means of ketoreductase or alcohol dehydrogenase is likewise known (US-A-2012/0064611). U.S. Pat. No. 6,645,746 discloses an amino acid sequence from *Candida magnoliae* which can be used for reducing tert-butyl-(5S)-6-chloro-5-hydroxy-3-oxohexanoate to tert-butyl-(3R,5S)-6-chloro-3,5-dihydroxyhexa-noate with the aid of NADP(H). In the description of this document the enzyme preferably co-expressed with glucose dehydrogenase from *Bacillus megaterium* is employed, the regeneration of the cofactor NADP(H) being carried out with the aid of glucose dehydrogenase and with glucose as a cosubstrate. WO-A-2004/1111083 describes a process for the enantioselective enzymatic reduction of ketones, in particular 2- and 3-oxo acid esters, wherein the reaction is catalysed by an oxidoreductase from *Pichia capsulata*. WO-A-2005/108593 describes a process for the preparation of 1-butanol in which 2-butanone is reduced with a carbonyl reductase, for example from *Candida parapsilosis*, and a coenzyme in a two-phase system. EP-A-2 061 880 discloses a process for the NADP(H)-dependent enzymatic preparation of alkenone derivatives from α,β-unsaturated alkynone derivatives, wherein the corresponding reductase is used in purified form or also in the form of the microorganism itself. EP-A-2 087 127 describes a process for the preparation of secol derivatives by enantioselective enzymatic reduction of secodione derivatives using an oxidoreductase/dehydrogenase in the presence of NADP(H).

In addition to the NADP(H)-dependent reduction of ketones and aldehydes, NADP(H)-dependent enzymes, so-called enoate reductases, are also used for enantiospecific reduction of enoates. Thus, Kataoka and colleagues have reported that by using an enoate reductase from *Candida macedoniensis* together with an NADP(H)-generating glucose dehydrogenase from *E. coli* ketoisophorone is reduced preoperatively to (6R)-levodione (Kataoka, Kotaka, Thiwthong, Wada, Nakamori, and Shimizu, *J. Biotechnol.*, 2004, 114, 1-9).

The use of NADP(H)-dependent enzymes in coupled systems where, for example, the reduction is followed by a cyclisation to the epoxide is furthermore described.

The use of (R)- or (S)-selective alcohol dehydrogenases in order to form the corresponding enantiomer and subsequently to achieve the base-induced cyclisation to the particular epoxide is thus described (CA 2 612 407).

Enzymatic provision of NADP(H) is also necessary if monooxygenases are employed, as in the case of the very thoroughly investigated monooxygenase P450 BM3 (CYP102A1) from *Bacillus megaterium* (*Appl. Microbiol. Biotechnol.* (2012) 95:357-367). This fatty acid hydroxylase oxidises a wide range of substrates, such as alkanes, alkenes and aromatic hydrocarbons. The monooxygenase catalyses the hydroxylation, but requires the stoichiometric supply of NADP(H).

NADP(H)-dependent enzymes are also employed for reductive amination, such as, for example, of 2-keto acids to the corresponding D-amino acid (WO-A-2006/113085), or of 6-aminocaproic acid from 2-ketopimelate (WO-A-2012/031911).

An overview of the most diverse uses of NADP(H)-dependent enzymes can be found, for example, in Hollmann, Arendsa and Holtmann (*Green Chemistry*, 2011, 13, 2285-2313), or also the textbook "*Industrial Biotransformations*" by Liese, Seelbach, and Wandrey (Wiley-VCH Verlag, 2006, ISBN: 3-527-31001-0).

Regardless of the concrete reaction for which NADP(H)-dependent enzymes are to be employed, it is initially a prerequisite to provide suitable enzymes which ensure high conversions and a high stereospecificity. A prerequisite of this in turn is screening for such enzymes, which can be carried out in various ways.

Thus, companies offer enzyme collections, which must then be tested to ascertain whether they convert the desired educt into the desired product, such as, for example, Novozymes A/S located in Bagsværd, Denmark. Desired enzymes can also be used by utilisation of the natural diversitivity. For example, by obtaining enzymes from organisms or metagenomic libraries, which in turn must be tested specifically. Diversitivity can also be established by man by mutagenising existing enzymes and then testing the enzymes obtained for modified substrate specificity. Examples for generating various enzymes by molecular techniques are disclosed in WO-A-2012/069434, where NADP(H)-dependent enzymes for the preparation of n-heterocyclic optically active alcohols are obtained. Similar processes for the preparation of 12α-hydroxysteroid dehydrogenase mutants are also described (EP-A-2 441 771). The preparation of large gene libraries which undergo an analysis with a high throughput comprises cloning of the gene library into replicable expression vectors, transforming of the suitable cells with the resulting vector library and expressing the combinantly obtained genes under conditions under which the detection of the desired activity and the isolation of the vector which codes for the gene of which the product has been detected are facilitated.

The direct test for desired conversion of the educt into the product has hitherto preferably been carried out in microtiter plates with 96, 384 or even 1,536 wells. These plates render possible parallel testing of 96, 384 or 1.536 enzymes. The product of the desired enzyme reaction can be determined directly by chromatography techniques. This method requires the removal of a sample from the 96, 384 or 1,536 wells and chromatographic separation for detection of the reaction products, which can be, for example, alcohols or carbonyl compounds. Needless to say, such a procedure is complex and time-consuming. Indirect tests are therefore often used. The fact that NADP(H) absorbs at 340 nm but NADP does not is thus utilised. The amount of NADP(H) consumed can in principle be determined via this. Alternatively, in the carbonyl reductase-catalysed oxidation of an alcohol the conversion of NADP into NADP(H) can also be measured in this way. In this and comparable reactions, the reduction of the cofactor NADP is determined by the increase in absorption at 340 nm. The intrinsic fluorescence of the reduced cofactor can equally also be used for the quantification. This is effected in microtiter reader apparatuses.

In another method for determining the NADP(H) consumption for detection of the enzymatic reductive transamination and also the reduction of ketones, the change in pH accompanying the NADP(H) consumption is determined by a colour indicator (U.S. Pat. No. 7,642,073). By a suitable choice of the colour indicator the wavelength of the change in colour can be determined, which in turn is determined in microtiter reader apparatuses.

Specific microtiter plate systems in which a screening in the microtiter plate format with up to 1,536 wells is carried out via membranes with specific analyte binding properties and liquid streams are also described (EP-A-1 628 768).

Attempts have also been made to make analytes more easily detectable by coupling with a detectable group, for example of a fluorophore. For this, the analyte is covalently bonded to a fluorescent group before the reaction is carried out. When the reaction is carried out and the analyte is correspondingly reacted, the fluorescence of the fluorescent group should change, for example by splitting off of the group or by a change in the structure of the analyte. The change in fluorescence is then a measure of the conversion of the analyte. A disadvantage of this, however, is that the fluorescent group often influences the reactivity of the analyte. WO-A-2007/131696 describes that by providing a fluorescent dyestuff and a macrocyclic structure in the sample to be investigated and measuring a fluorescence property of the fluorescent dyestuff at two points in time at least, the analyte concentration can be determined. The macrocyclic structure thereby binds the dyestuff and within the concentration range to be investigated for the analyte this displaces the fluorescent dyestuff from the macrocyclic structure.

In the in vitro screening set-ups known from the prior art for isolating new NADP(H)-consuming enzymes or NADP (H)-consuming enzymes from gene libraries having a modified substrate specificity, a general disadvantage is that microtiter plate systems which do not render possible high throughput screening such as is possible, for example, with fluorescence-activated cell sorting (FACS) are used.

Furthermore, in in vitro screening set-ups for isolating new NADP(H)-dependent enzymes, cell lysates are often employed as a potential source of new enzymes, since isolation in the pure form is operationally difficult. The problem of such lysates or preparations in routine screening for new NADP(H)-dependent enzymes is, however, that the reaction batch typically contains insoluble material or other enzymes which interact with the NADP(H). This leads to high blank values or also a modified non-specific absorption at 340 nm, which reduces the accuracy and the value of the absorption measurement. The same applies to fluorescence measurement of the cofactor, which is likewise made difficult by insoluble material.

The present invention was based on the object of overcoming the disadvantages emerging from the prior art in connection with isolating new NADP(H)-dependent enzymes.

In particular, the present invention was based on the object of providing a tool which can be used in order to be able to isolate in a high throughput screening, for example by means of FACS, from a cell suspension in the simplest possible manner those cells which possibly express new NADP(H)-dependent enzymes. In particular, the isolation of these cells should comprise no cell breakdown, and in particular also no analytical determination of the concentration of particular educts, products or cofactors.

The present invention was moreover based on the objet of providing a cell which, after a gene for a potential NADP (H)-dependent enzyme, for example in the form of a plasmid, has been introduced into the cell, can be analysed particularly easily, and in particular without the need for a cell breakdown, as to whether the gene expressed by this cell in fact codes for an NADP(H)-dependent enzyme. A cell identified in this manner should moreover should be able to be separated off as far as possible in a targeted manner in a high throughput screening, for example by means of FACS, from a large number of cells, for example from a cell suspension.

A contribution towards achieving the abovementioned objects is made by an NADP(H) nanosensor comprising i) a nucleic acid sequence to which a regulator is capable of binding, wherein the oxidation state of the regulator depends on the NADP(H) availability;

ii) a promoter sequence following the nucleic acid sequence i), to which an RNA polymerase is capable of binding, wherein the affinity of the RNA polymerase for the promoter sequence is influenced by the oxidation state of the regulator;

iii) a nucleic acid sequence which is under the control of the promoter sequence ii) and which codes for an autofluorescent protein.

It has been found, surprisingly, that using the NADP(H) nanosensor according to the invention the intracellular NADP or NADP(H) concentration, and therefore indirectly the activity of NADP(H)-dependent enzymes in a cell, can be determined in vivo particularly easily. If a cell containing the NADP(H) nanosensor according to the invention is characterised by a high activity of NADP(H)-dependent enzymes, the concentration of NADP is correspondingly high (and the NADP(H) concentration correspondingly low). Depending on this reduction state of the cell, the regulator is capable of influencing the affinity of the RNA polymerase for the promoter controlling the expression of the autofluorescent protein, or the stability of the mRNA coding for the autofluorescent protein. The expression of the autofluorescent protein is thus controlled according to the reduction state of the cell, and in turn can be monitored in a simple manner by irradiation with electromagnetic radiation, which excites the autofluorescent protein to emission of light. The emission of light by the cells is thus an indicator for the reduction state of the cell and consequently for the extent of the expression of NADP(H)-dependent enzymes.

According to a preferred embodiment of the NADP(H) nanosensor according to the invention, the regulator is the Sox regulator (SoxR) and the promoter sequence is the soxS promoter sequence. The gene for SoxR from *E. coli* K12 is deposited under accession numbers b4063, ECK4055 in the National Center for Biotechnology Information (NCBI) database of the National Library of Medicine (Bethesda, Md., USA). SoxR contains two [2Fe-2S] clusters, which are essential for the transcription activity. Each SoxR polypeptide contains a [2Fe-2S] cluster which detects the reduction state of the cell. Both Fe-SoxR and apo-SoxR bind to the promoter region, but only Fe-SoxR contributes towards promoter activation in the oxidised form. The redox state of the iron-sulphur cluster regulates the SoxR activity. The target gene of SoxR is the adjacent soxS, the sequence of which is deposited under numbers b4062, ECK4054 in the National Center for Biotechnology Information (NCBI) database of the National Library of Medicine (Bethesda, Md., USA). The reduction state of the cell can be promoted, if appropriate, by NADP(H)-dependent reductases, such as Rsx or RseC.

In this connection it is furthermore preferable for components i) and ii) to be formed by the intergenic region from *E. coli*, which is located between soxR and soxS and which comprises the SoxR binding sequence, the soxS promoter sequence following the SoxR binding sequence and a sequence following the soxS promoter sequence, which corresponds at the level of the mRNA to a ribosome binding site, or by a nucleic acid sequence homologous to this. Components i) and ii) in this context are preferably formed by a nucleic acid sequence selected from the group consisting of:

a) a nucleic acid sequence according to SEQ. ID. No. 01,
b) a nucleic acid sequence which has an identity of at least 70%, preferably at least 80%, still more preferably at least 85%, still more preferably at least 90%, still more preferably at least 91%, still more preferably at least 92%, still more preferably at least 93%, still more preferably at least 94%, still more preferably at least 95%, still more preferably at least 96%, still more preferably at least 97%, still more preferably at least 98% and most preferably at least 99% to the nucleic acid sequence of a), the nucleic acid sequence being able to bind SoxR such that the affinity of the RNA polymerase for the soxS promoter depends on the oxidation state of SoxR, and
c) a nucleic acid sequence which is capable of hybridising under stringent conditions with a complementary nucleic acid sequence according to a) or b), the nucleic acid sequence being able to bind SoxR such that the affinity of the RNA polymerase for the soxS promoter depends on the oxidation state of SoxR.

According to a first variant of this particularly preferred embodiment of the NADP(H) nanosensor according to the invention, this comprises
(α1) the *E. coli* gene for SoxR (soxR) or a nucleic acid sequence homologous to this;
(α2) the intergenic region from *E. coli*, following (α1), which is located between soxR and soxS and which comprises the SoxR binding sequence, the soxS promoter sequence following the SoxR binding sequence and a sequence following the soxS promoter sequence, which at the level of the mRNA corresponds to a ribosome binding site, or a nucleic acid sequence homologous to this, as defined above, as components i) and ii);
(α3) if appropriate a part sequence, following (α2), of the soxS gene from *E. coli* or a nucleic acid sequence homologous to this:
(α4) a nucleic acid sequence, which codes for an autofluorescent protein, following (α2) or (α3), preferably (α3) and which is under the control of the soxS promoter sequence, as component iii).

The wording "a sequence b) following a sequence a)" as used above and also in the following is to be understood according to the invention as meaning that the sequence b) does not necessarily have to be bonded directly to the sequence a), but that an intermediate sequence can also be located between sequence a) and sequence b).

According to this particular embodiment, the NADP(H) nanosensor comprises as component (α1) the *E. coli* gene for soxR (soxR) or a nucleic acid sequence homologous to this, component (α1) preferably being selected from the group consisting of:

a) a nucleic acid sequence according to SEQ. ID. No. 02,
b) a nucleic acid sequence coding for a polypeptide with an amino acid sequence according to SEQ. ID. No. 03,
c) a nucleic acid sequence which has an identity of at least 70%, preferably at least 80%, still more preferably at least 85%, still more preferably at least 90%, still more preferably at least 91%, still more preferably at least 92%, still more preferably at least 93%, still more preferably at least 94%, still more preferably at least 95%, still more preferably at least 96%, still more preferably at least 97%, still more preferably at least 98% and most preferably at least 99% to the nucleic acid sequence of a) or b), the nucleic acid sequence coding for a polypeptide which is capable of binding to the SoxR binding sequence in the intergenic region from *E. coli* which is located between soxR and soxS and the oxidation state thereof being capable of influencing the affinity of the RNA polymerase for the promoter sequence likewise located in the intergenic region from *E. coli*,
d) a nucleic acid sequence coding for a polypeptide which has a homology of at least 70%, preferably at least 80%, still more preferably at least 85%, still more preferably at least 90%, still more preferably at least 91%, still more preferably at least 92%, still more preferably at least 93%, still more preferably at least 94%, still more preferably at least 95%, still more preferably at least 96%, still more preferably at least 97%, still more preferably at least 98% and most preferably at least 99% to SEQ. ID. No. 03, the nucleic acid sequence coding for a polypeptide which is capable of binding to the SoxR binding sequence in the intergenic region from *E. coli* which is located between soxR and soxS and the oxidation state thereof being capable of influencing the affinity of the RNA polymerase for the promoter sequence likewise located in the intergenic region from *E. coli*, and
e) a nucleic acid sequence which is capable of hybridising under stringent conditions with a complementary nucleic acid sequence according to one of groups a) to d), the nucleic acid sequence coding for a polypeptide which is capable of binding to the SoxR binding sequence in the intergenic region from *E. coli* which is located between soxR and soxS and the oxidation state thereof being capable of influencing the affinity of the RNA polymerase for the promoter sequence likewise located in the intergenic region from *E. coli*.

The expression "homology" (or "identity") as used herein can be defined by the equation H (%)=[1−V/X]×100, wherein H denotes homology, X is the total number of nucleobases/amino acids of the comparison sequence and V is the number of different nucleobases/amino acids of the sequence to be considered, with respect to the comparison sequence. In all cases, the term nucleic acid sequences which code for polypeptides includes all sequences which appear to be possible according to the proviso of degeneration of the genetic code.

The identity of nucleic acid sequences can be identified using a sequence comparison program (BLAST. Altschul et al. *J. Mol. Biol.* 1990, 215, 403-410). The percentage homology between two amino acid sequences can likewise be readily determined by the person skilled in the art using methods know from the prior art. A suitable program which can be employed according to the invention is BLASTp (Altschul et al., 1997; "Gapped BLAST and PSI-BLAST: a new generation of protein database search programs"; *Nucleic Acids Res.* 25(17): 3389-3402).

The person skilled in the art can find instructions for hybridisation inter alia in the handbook "*The DIG System User's Guide for Filter Hybridization*" of Boehringer Mannheim GmbH (Mannheim, Germany, 1993) and in Liebl et al. (*International Journal of Systematic Bacteriology* 41: 255-260 (1991)). The hybridisation takes place under stringent conditions, that is to say only hybrids in which the probe, for example the nucleotide sequence complementary to soxR or soxS or the intergenic region of soxRS from *E. coli*, and the target sequence, i.e. the polynucleotides treated with the probe, are at least 70% identical. It is known that the stringency of the hybridisation including the washing steps is influenced or determined by varying the buffer composition, the temperature and the salt concentration. The hybridisation reaction is in general carried out at a relatively low stringency compared with the washing steps (Hybaid Hybridisation Guide, Hybaid Limited, Teddington, UK, 1996). For the hybridisation reaction, for example, a buffer corresponding to 5×SSC buffer can be employed at a temperature of approx. 50° C.-68° C. In this context probes can also hybridise with polynucleotides which have less than 70% identity to the sequence of the probe. Such hybrids are less stable and are removed by washing under stringent conditions. This can be achieved, for example, by lowering the salt concentration to 2×SSC and if appropriate subsequently 0.5×SSC (The DIG System User's Guide for Filter Hybridization, Boehringer Mannheim, Mannheim, Germany, 1995), a temperature of approx. 50° C.-68° C. approx. 52° C.-68° C. approx. 54° C.-68° C., approx. 56° C.-68° C., approx. 58° C.-68° C. approx. 60° C.-68° C. approx. 62° C.-68° C. approx. 64° C.-68° C., approx. 66° C.-68° C. being established. Preferably, the washing steps are carried out at temperatures of approx. 62° C.-68° C., preferably of 64° C.-68° C. or approx. 66° C.-68° C. particularly preferably of approx. 66° C.-68° C. It is possible, where appropriate, to lower the salt concentration to a concentration corresponding to 0.2×SSC or 0.1×SSC. By increasing the hybridisation temperature stepwise in steps of approx. 1-2° C. from 50° C. to 68° C. polynucleotide fragments which code for soxR or soxS or the intergenic region of soxRS which have, for example, at least 70% or at least 80% or at least 90% to 95% or at least 96% to 98% or at least 99% identity to the sequence of the probe employed can be isolated. Further instructions for the hybridisation are obtainable on the market in the form of so-called kits (e.g. DIG Easy Hyb from Roche Diagnostics GmbH, Mannheim, Germany, catalogue no. 1603558).

The NADP(H) nanosensor according to this particular embodiment comprises as component ($\alpha$4) a nucleic acid sequence which codes for an autofluorescent protein and which follows ($\alpha$2) or $\alpha$3), preferably the target gene soxS ($\alpha$3), in particular the first 5 to 200 nucleotides of the target gene soxS, and is under the control the soxS promoter sequence, as component iii).

According to the invention, the gene sequence according to component iii) coding for the autofluorescent protein is under the control of the promoter sequence ii) (according to the first variant described above for the particular embodiment of the NADP(H) nanosensor according to the invention, the gene sequence ($\alpha$4) coding for the autofluorescent protein is under the control of the soxS promoter sequence). The term "under control of the promoter sequence" in this context is preferably to be understood as meaning that the gene sequence coding for the auto fluorescent protein is functionally linked to the promoter. The promoter and the gene sequence coding for the autofluorescent protein are functionally linked if these two sequences and optionally further regulative elements, such as, for example, a terminator or a ribosome binding site, are arranged sequentially such that each of the regulative elements can fulfil its function in the transgenic expression of the nucleic acid sequence. For this, a direct linking in the chemical sense is not absolutely necessary. Genetic control sequences, such as, for example, enhancer sequences, can also exert their function on the target sequence from further removed positions or even from other DNA molecules. Arrangements in which the gene sequence coding for the autofluorescent protein is positioned alter the promoter sequence (i.e. at the 3' end), so that the two sequences are bonded covalently to one another, are preferred. Preferably, in this context the distance between the gene sequence coding for the autofluorescent protein and the promoter sequence is less than 200 base pairs, particularly preferably less than 100 base pairs, very particularly preferably less than 50 base pairs. It is also possible for the gene sequence coding for the autofluorescent protein and the promoter to be linked functionally to one another such that there is still a part sequence of the homologous gene (that is to say that gene of which the expression in the wild-type cell is regulated by the promoter) between these two gene sequences (according to the particular embodiment of the NADP(H) nanosensor described above, pans of the soxS gene according to component ($\alpha$3) can accordingly be between the soxS promoter sequence and the nucleic acid sequence ($\alpha$4) coding for the autofluorescent protein). In the expression of such a DNA construct, a fusion protein is obtained from the autofluorescent protein and the amino acid sequence which is coded by the corresponding part sequence of the homologous gene (=translational fusion). The lengths of such part sequences of the homologous gene are not critical as long as the functional capacity of the autofluorescent protein, that is to say its property of being fluorescent when excited with light of a particular wavelength, is not noticeably impaired. In the case of the particular embodiment of the NADP(H) nanosensor according to the invention described above, the soxS part sequence ($\alpha$3) preferably comprises at least the first 5 nucleotides, still more preferably at least the first 10 nucleotides and still more preferably at least the first 20 nucleotides, but preferably at most the first 200 nucleotides, still more preferably at most the first 150 nucleotides and still more preferably at most the first 100 nucleotides of the soxS gene.

The nucleic acid sequence (iii) (or ($\alpha$4) and ($\beta$4)) coding for an autofluorescent protein preferably comprises genes coding for fluorescent proteins which code for fluorescent proteins of the genus *Aequora*, such as green fluorescent protein (GFP), and variants thereof which are fluorescent in a different wavelength range (e.g. yellow fluorescent protein (YFP), blue fluorescent protein (BFP), cyan fluorescent protein (CFP)) or of which the fluorescence is enhanced (e.g. enhanced green fluorescent protein (EGFP), enhanced yellow fluorescent protein (EYFP), enhanced blue fluorescent protein (EBFP) or enhanced cyan fluorescent protein (ECFP). Gene sequences which code for other autofluorescent proteins. e.g. DsRed, HcRed, AsRed, AmCyan, ZsGreen, AcGFP, ZsYellow, such as are known from BD Biosciences, Franklin Lakes, USA, can furthermore also be used according to the invention. A photoreceptor protein which contains a so-called LOV domain can likewise be used. The particularly preferred autofluorescent protein in this context is EYFP.

According to a second variant of the particularly preferred embodiment of the NADP(H) nanosensor according to the invention, this comprises (β1) the *E. coli* gene for SoxR (soxR) or a nucleic acid sequence homologous to this;

(β2) the intergenic region from *E. coli*, following (β1), which is located between soxR and soxS and which comprises the SoxR binding sequence, the soxS promoter sequence following the SoxR binding sequence and a sequence following the soxS promoter sequence which at the level of the mRNA corresponds to a ribosome binding site, or a nucleic acid sequence homologous to this, as defined above, as components i) and ii);

(β3) the sequence of the soxS gene from *E. coli* following (β2) and under the control of the soxS promoter sequence, a part sequence of this gene or a nucleic acid sequence homologous to this;

(β') a further sequence following (β3) which at the mRNA level corresponds to a ribosome binding site;

(β4) a nucleic acid sequence, which codes for an autofluorescent protein, following (β') and which is under the control of the soxS promoter sequence, as component iii).

Components (β1), (β2, (β3) and (β4) which are preferred are those components which have already been mentioned above as preferred components (α1), (α2), (α3) and (α4) in connection with the first variant of the particularly preferred embodiment of the NADP(H) nanosensor according to the invention, During the expression of such a DNA construct, SoxS or a fragment of this protein and, separately from this, the autofluorescent protein are formed (=transcriptional fusion).

A contribution towards achieving the abovementioned objects is also made by a cell comprising an NADP(H) nanosensor according to the invention. In this context the NADP(H) nanosensor according to the invention can be present in the cell in the episomal or chromosomal form.

Examples of suitable cells which may be mentioned in particular are *Escherichia coli, Pseudomonas fluorescens, Corynebacterium glutamicum, Bacillus subtilis* or another *Eubacterium*, or also *Saccharomyces cerevisiae* or another yeast.

The cells according to the invention are suitable for establishing whether particular gene sequences code for an NADP(H)-dependent enzyme. For this, the gene coding for a potential NADP(H)-dependent enzyme is introduced into the cell and expressed. As described above, the emission of light by the cells is an indicator for the reduction state of the cell and consequently for the extent of the expression of NADP(H)-dependent enzymes.

In this context, according to the invention an "NADP(H)-dependent enzyme" is understood as meaning any enzyme which is involved in at least a part step of the conversion of a substrate into a reaction product which is chemically different from this substrate, NADP(H) being involved as a cofactor in at least one part step of this conversion.

According to a preferred embodiment of the cell according to the invention, this accordingly furthermore comprises, in addition to the NADP(H) nanosensor according to the invention, a plasmid with an optionally mutated gene which codes for an NADP(H)-dependent enzyme. The NADP(H)-dependent enzyme in this context is preferably selected from the group consisting of alcohol dehydrogenases, aldehyde dehydrogenases, lactate dehydrogenases, enoate reductases, epoxide reductases, diaminopimelate dehydrogenases, amino acid dehydrogenases, aldehyde oxidoreductases, alkane reductases, amine reductases, epoxide dehydrogenases, carboxylic acid dehydrogenases, hydroxy acid ketoreductases and hydroxy acid dehalogenases.

A contribution towards achieving the abovementioned objects is also made by a recombinant cell comprising a nucleic acid sequence coding for an autofluorescent protein, wherein the extent of the expression of the autofluorescent protein in the cell depends on the intracellular NADP(H) availability. In this connection particularly preferred cells are the cells described above, in particular cells comprising the NADP(H) sensor according to the invention.

A contribution towards achieving the abovementioned objects is also made by a method for isolating genes which code for NADP(H)-dependent enzymes, comprising the method steps:

(I) providing an NADP(H) nanosensor according to the invention;

(II) introducing the NADP(H) nanosensor into a cell;

(III) introducing a gene which may code for an NADP(H)-dependent enzyme into individual cells of a cell suspension of the cells obtained in method step (II);

(IV) incubating the cells with a substrate for the NADP(H)-dependent enzyme;

(V) identifying individual cells in the cell suspension with an increased activity of NADP(H)-dependent enzymes by detection of the intracellular fluorescence activity;

(VI) separating off the identified cells from the cell suspension;

(VII) isolating the genes coding for an NADP(H)-dependent enzyme in the identified cells.

New NADP(H)-dependent enzymes and mutated NADP(H)-dependent enzymes with increased or modified substrate recognition can be isolated with the aid of this method.

Sensors and cells which are preferred as the NADP(H) sensor and as the cell are those which have already been described above as preferred sensors or cells in connection with the sensor according to the invention or the cell according to the invention.

In method steps (I) and (II) a cell according to the invention is first prepared by introducing the NADP(H) nanosensor according to the invention into a cell, it being possible for this introduction to be carried out in the episomal or chromosomal form.

In method step (III) of the method according to the invention a gene which may code for an NADP(H)-dependent enzyme is then introduced into individual cells of a cell suspension of the cells obtained in method step (II), it being possible for the gene to be, in particular, a mutated, plasmid-coded gene of an NADP(H)-dependent enzyme. To introduce the site-nonspecific mutations into the plasmid-coded genes of the NADP(H)-dependent enzymes to increase the diversity, an in vitro mutagenesis is preferably carried out with the aid of an error-prone polymerase chain reaction (PCR) and an amplification technique. In this context the gene to be mutated is subjected to a PCR using a polymerase which, depending on the conditions of the reaction, incorporates individual bases incorrectly into the synthesized genes (Tindall, K. R, and T. A. Kunkel: "Fidelity of DNA synthesis by the *Thermus aquaticus* DNA polymerase"; Biochemistry, 1988, 27 (16), pages 6008-13). A frequent variant of this method comprises the use of manganese(II) ions or of nucleotide analogues in the PCR batch (Cadwell R. C et al. (1992); PCR Methods Appl. (2), pages 28-33/ Leung D. W. et al. (1989) Techniques (I), pages 11-15). These techniques for introduction of mutations are called "error-prone PCR (epPCR)" (Labrou N E: "Random mutagenesis methods for in vitro directed enzyme evolution": Curr. Protein. Pept. Sci. 2010 (11), pages: 91-100). The mutations can be, for example, point mutations, and e.g. substitutions, deletions or insertions can be generated by the polymerase. The mutation rate is between 1-40 mutations per 1 kb, preferably 1-5 mutations per 1 kb. However, mutations can also be produced with the aid of saturation mutagenesis using the Stratagene QuikChange Kit (La Jolla, Calif., USA), or also using a method called SeSam (EP 1 670 914 B1), with which any existing nucleotide is transferred under saturation into any possible nucleotide.

Possible NADP(H)-dependent enzymes of which the activity can be analysed with the nanosensor-carrying host in a high throughput are, for example, 1,2-dehydroreticulin reductases (1.5.1.27), 2-enoyl-CoA reductase (1.3.1.10), 2-enoyl-CoA reductases (1.3.1.39), alkenal/one oxidoreductases (1.3.1.74) cytochrome P450 reductase (1.6.2.4), NADP (H) dehydrogenases (1.6.99.1), NADP(H) dehydrogenases (flavin) (1.6.8.2), NADP(H) dehydrogenases (quinone) (1.6.5.10), NADP(H)-dependent 1,5-anhydro-D-fructose reductases (1.1.1.263), NADP(H)-dependent cytochrome P450 reductases (1.6.2.4), diaphorases (1.6.99.1), DT-diaphorases (1.6.5.5), ferredoxin reductases (1.18.1.2), NADP (H) oxidases (1.6.3.1, 1.6.5.10, 1.6.3.1, 1.6.3.1, 1.6.3.1), P450 oxidoreductase (1.6.2.4), P450 reductase (1.6.2.4), peroxidase (1.11.1.2), quinone acceptor oxidoreductase (1.6.5.5), quinone oxidoreductase (1.6.5.10), NADP(H)-specific FMN reductase (1.5.1.38), thioredoxin reductase (1.8.1.9), transhydrogenase (1.6.1.2), NADP(H)-aldehyde reductase (1.1.1.2), aldopentose reductase (1.1.1.21), NADP (H)-aldose reductase (1.1.1.21), NADP(H)-carbonyl reductase (1.1.1.184), NADP(H)-CYP reductase (1.6.2.4), NADP (H)-cytochrome c oxidoreductase (1.6.2.4), NADP(H)-cytochrome c reductase (1.1.1.2), NADP(H)-cytochrome f reductase (1.6.2.5), NADP(H)-cytochrome P450 reductase (1.6.2.4) and NADP(H)-cytochrome P450 reductase (1.14.13.68).

The plasmids which contain mutations in genes of the NADP(H)-dependent enzymes are then introduced into the microorganism, such as, for example, *E. coli* or *C. glutamicum*, by transformation. In this context the term "transformation" includes all methods for transfer of polynucleotides, in particular DNA, into a desired bacterium. These include inter alia the use of isolated DNA in transformation, electro transformation or electroporation, transfer by cell contact, as in conjugation, or transfer of DNA by means of particle bombardment.

After in process step (III) a gene which optionally codes for an NADP(H)-dependent enzyme has been introduced into individual cells of a cell suspension from the cells obtained in method (II) (and expressed), the cells are then incubated in method step (IV) with a substrate for an NADP(H)-dependent enzyme, and in method step (V) individual cells in the cell suspension with an increased activity of NADP(H)-dependent enzymes are then identified by detection of the intracellular fluorescence activity. For this, the cell suspension is exposed to electromagnetic radiation in that frequency which excites the autofluorescent protein of the NADP(H) nanosensor to emission of light.

In method step (VI) the identified cells are then separated off from the cell suspension, this separating off preferably being carried out by means of flow cytometry (FACS=fluorescence activated cell sorting), very particularly preferably by means of high throughput flow cytometry (HT-FACS=high throughput fluorescence activated cell sorting). Details on the analysis of cell suspensions by means of flow cytometry can be found, for example, in Sack U, Tarnok A. Rothe G (eds.): Zelluläre Diagnostik, Grundlagen, Methoden und klinische Anwendungen der Durchflusszytometric, Basel, Karger, 2007, pages 27-70.

In method step (VII) the genes coding for an NADP(H)-dependent enzyme in the identified cells are then isolated and if appropriate analysed, for example by isolating the enzyme-carrying plasmids from the cells which have been separated off and identifying and verifying, by sequencing, their mutation which lead to modified fluorescence.

A contribution towards achieving the abovementioned objects is also made by the use of the NADP(H) nanosensor according to the invention for identifying, in vivo, genes which code for an NADP(H)-dependent enzyme.

The invention is now explained in more detail with the aid of figures and non-limiting examples.

Figure 1:
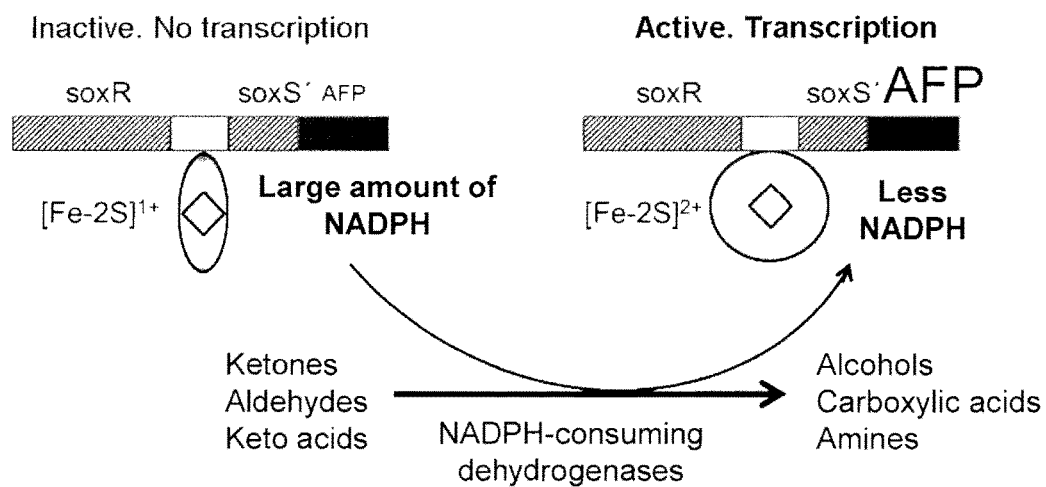
FIG. 1 shows the mode of functioning of the NADP(H) nanosensor according to the invention by the example of the particularly preferred embodiment described above.

According to FIG. 1, the NADP(H) nanosensor can comprise the *E. coli* gene for SoxR (soxR), the intergenic region from *E. coli* following this, which is located between soxR and soxS and which comprises the soxR binding sequence and the soxS promoter sequence following the SoxR binding sequence, a part sequence of the soxS gene from *E. coli* (soxS') following this and a nucleic acid sequence following this, under the control of the soxS promoter sequence, which codes for a autofluorescent protein (AFP). At a high cytosol NADP(H) concentration (top left in FIG. 1), the [2Fe-2S] clusters (rhomb) are present in a form reduced by SoxR bound to the promoter. At a low NADP(H) availability (top right in FIG. 1), the [2Fe-2S] clusters are oxidised, and the resulting distortion of the soxS promoter region renders transcription initiation of the target gene possible for the RNA polymerase. According to the invention the native target gene soxS is fused with an autofluorescent protein (AFP). NADP(H)-dependent enzymes cause increased expression of soxS'-AFP by consumption of NADP(H) and therefore increased fluorescence of cells as a result of increased NADP(H) consumption.

Figure 3:
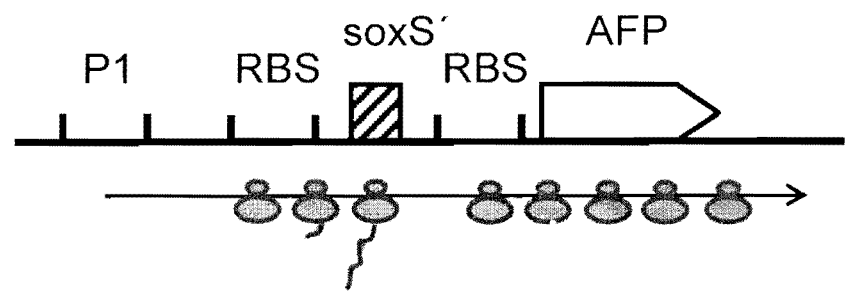
FIG. 3 shows a diagram of the formation of the autofluorescent protein as transcriptional (top) and translational (bottom) fusion.
Figure 3:
Figure 3:
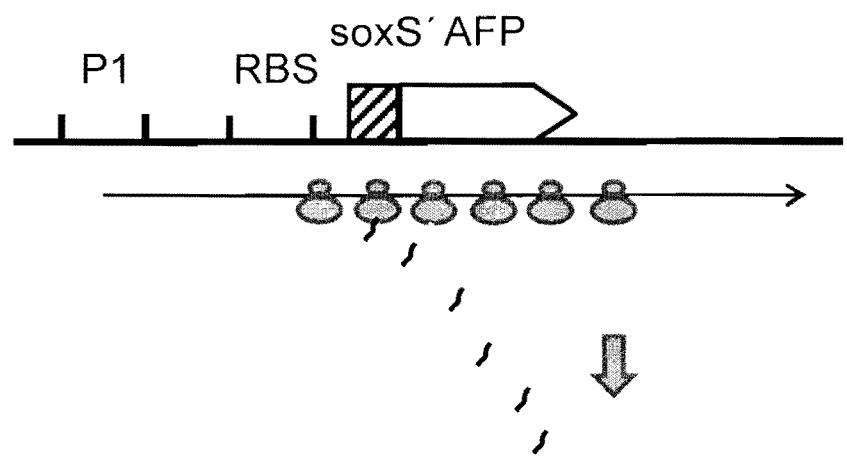

FIG. 3 shows at the top the transcriptional and at the bottom the translational fusion. In both cases a transcript is formed by the promoter PI, which is, for example, the soxS promoter controlled by SoxR. Whereas during transcriptional fusion two separate peptides are formed due to a second ribosome binding site (RBS), during translational fusion a single peptide is formed, the fusion protein, in which the autofluorescent protein contains additional amino acid sequences.

EXAMPLES

Example 1

Construction of the NADPH Nanosensor (Transcriptional Fusion)

With the primer pairs SoxS_for_SphI (SEQ. ID. No. 04) and SoxR_rev_SalI (SEQ. ID. No. 05) and chromosomal DNA from E. coli DIS5α as the template, the gene soxR as amplified together with the intergenic region of soxR-soxS and the first 63 nucleotides of soxS.

```
SoxS_for_SphI:
ATCTGCATGCTTACGGCTGGCAATATGCTCGTC

SoxR rev SalI:
GCTAGTCGACCAAACTAAACCGCCCTTGTG
```

With the primer pairs EYFP_for_SphI (SEQ. ID. No. 06) and EYFP_rev_ClaI (SEQ. ID. No. 07) and the vector pSenLys as the template, the gene eyfp was amplified together with a ribosome binding site. The vector pSenLys is described in the patent application WO-A-2011/138006.

```
EYFP_for_SphI:
AGAGGCATGCAAGGAGAATTACATGGTGAGCAAGGGCGAGG

EYFP_rev_ClaI:
GCGCATCGATTTATTACTTGTACAGCTCGTCCATG
```

The vector pBtacLbadh codes for the NADPH-dependent alcohol dehydrogenase from Lactobacillus brevis (Lbadh). It is described in Ernst et al. (Ernst M, Kaup B, Müller M, Bringer-Meyer S, Sahm H, Appl. Microbiol. Biotechnol. 2005, 66(6), pages 629-34). The vector pBtacLbadh was treated with the restriction enzymes SalI and ClaI, and the vector fragment~5.0 kb in size was isolated from the agarose gel and treated with alkaline phosphatase and purified with the QIAquick Gel Extraction Kit (cat. no. 28704) from Quiagen (Hilden, Germany). The two PCR products and the vector were then ligated by means of T4 DNA ligase from New England Biolabs (New England Biolabs, 240 County Road, Ipswich, Mass. 01938-2723). The ligation batch was transformed directly into the E. coli strain DH5α. Selection of plasmid-carrying cells was carried out by plating out the transformation batch on LB agar (Sambrook et al.: "Molecular cloning: a laboratory manual", 2nd edition, Cold Spring Harbor Laboratory Press, Cold Spring Harbor, N.Y.), which had been supplemented with 50 mg/l of ampicillin. Plasmid DNA was isolated from a transformant and checked by treatment with the restriction enzyme BamHI with subsequent agarose gel electrophoresis. The plasmid was called pSenSox and is deposited as the sequence SEQ. ID. No. 08.

pSennegK was created as a derivative with modified alcohol dehydrogenase. Lbadh. For this, with the primers ADH_negK_for (SEQ. ID. No. 09) and ADH_negK_rev (SEQ. ID. No. 10) and again pBtacLbadh as the template, an inactive Lbadh was amplified with an alcohol dehydrogenase deleted by 221 bp. The resulting fragment was ligated with the ~5.7 kb size vector fragment containing the gene eyfp together with a ribosome binding site. The sequence of the resulting vector is deposited as SEQ. ID. No. 11.

```
ADH_negK_for:
ACAAGAATTCGCTAAGAGTGTCGGCACTCC

ADH_negK_rev:
GGCCAAGCTTCCGAAGAAGACACCATCAAG
``` pSen-L194S was created as a further derivative with modified alcohol dehydrogenase. Lbadh. For this, with the primers L194S_for (SEQ. ID. No. 12) and L194S_rev (SEQ. ID. No. 13), pSenSox was amplified as a template for targeted insertion of the mutation. The plasmid generated was verified by means of sequencing. The sequence of the resulting vector is deposited as SEQ. ID. No. 14.

```
L194S_for:
CTGGCTACATCAAGCACCATCTGTTGATG

L194S_rev:
CGGCCCCTGGTAGGTCATCAACAGATGGTG
``` pSen-L194A was created as a further derivative with modified alcohol dehydrogenase, Lbadh. For this, with the primers L194A_for (SEQ. ID. No. 15) and L194A_rev (SEQ. ID. No. 16), pSenSox was amplified as a template for targeted insertion of the mutation. The plasmid generated was verified by means of sequencing. The sequence of the resulting vector is deposited as SEQ. ID. No. 17.

```
L194A_for:
CTGGCTACATCAAGACACCAGCGGTTGATG

L194A_rev:
CGGCCCCTGGTAGGTCATCAACCGCTGGTG
```

Example 2

Use of the NADP(H) Nanosensor for Monitoring Alcohol Dehydrogenase-Dependent Product Formation E. coli BL21(DE3) (Life Technologies GmbH, Frankfurter Straße 129B, 64293 Darmstadt) was transformed with the plasmid pSenSox. 5 ml of 2×YT medium (16 g/l of tryptone, 10 g/l of yeast extract. 5 g/l of NaCl) was inoculated with an individual colony and the culture was incubated overnight at 37° C. and 130 rpm. Using this preculture the main culture was inoculated to an OD of 0.05 in 50 ml of 2×TY and was incubated at 37° C. and 130 rpm. At the OD of 0.31 mM IPTG was added and the culture was incubated for a further 3 hours to an OD of 5-6.

Figure 2:
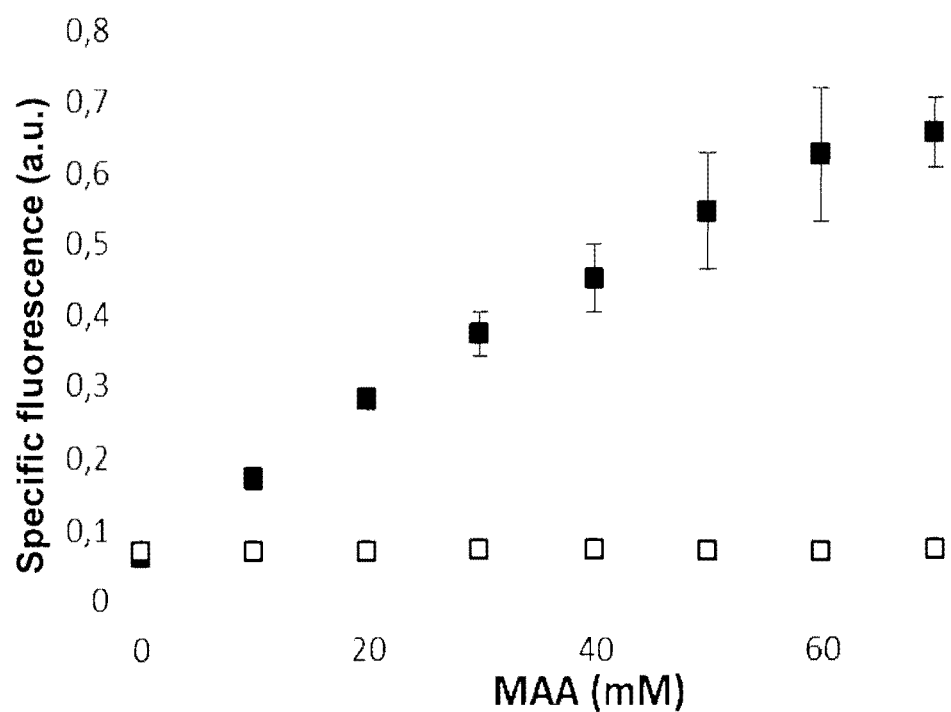
FIG. 2 shows the specific fluorescence of the *E. coli* BL21(DE3) cells, prepared in Example 3, with the NADP (H) nanosensor according to the invention (pSensox) and expressed alcohol dehydrogenase (Lbadh) (solid squares). The fluorescence of the nanosensor pSennegK with inactive alcohol dehydrogenase is shown as a control (open squares).

0.9 ml portions of the cell suspension were then introduced into a reaction vessel of the Flowerplate microtiter plate (48-well) of the BioLector cultivation system (m2plabs GmbH, Aachen, Germany). Methyl acetoacetate (MAA) was added to the cell suspension in increasing concentration in a constant volume of 0.1 ml. The Flowerplate microtiter plate was then incubated at 30° C. 1,200 rpm, shaking radius 3 mm. In the BioLector cultivation system the growth was recorded online as scattered light at 620 nm, and the fluorescence of the culture was recorded continuously at an excitation wavelength of 485 nm and an emission wavelength of 520 nm. The specific fluorescence after 10 hours was plotted against the amount of MAA added and is shown in FIG. 2 (0-70 mM methyl acetoacetate was added to individual batches and after 10 hours the specific fluorescence was determined, this being shown as squares filled with black; E. coli BL21(DE3) pSennegK with inactive Lbadh served as a negative control (empty squares). FIG. 2 shows an increase in the fluorescence with increasing MAA concentration. This increase is due to pSenSox, since a control reaction with the plasmid pSennegK with inactive alcohol dehydrogenase, which, however, is otherwise identical to pSenSox, causes no increase in fluorescence.

Example 3

Use of the NADP(H) Nanosensor for Determining Different Alcohol Dehydrogenase Activities The strain E. coli BL21(DE3) (Life Technologies GmbH, Frankfurter Stralβe 129B, 64293 Darmstadt) was transformed in each case with pSennegK, pSen-L194S and pSen-L194A. In addition, the strain E. coli BL21(DE3) pSenSox described in Example 2 was transformed with pET28a as the second plasmid. The vector mentioned last was obtained from Novagen (Life Technologies GmbH. Frankfurter Straβe 129B, 64293 Darmstadt), 5 ml of 2×YT medium (16 g/l of tryptone, 10 g/l of yeast extract, 5 g/l of NaCl) was inoculated with an individual colony of the particular strain and the culture was incubated overnight at 37° C. and 130 rpm. Using this preculture the main culture was inoculated to an OD of 0.05 in 50 ml of 2×TY and was incubated at 37° C. and 130 rpm. At the OD of 0.3 no IPTG was added or 1 mM IPTG was added to the strain E. coli BL21(DE3) pSenSox and the culture was incubated for a further 3 hours to an OD of 5-6.

As described in Example 2, 0.9 mil portions of the cells were then each introduced into a reaction vessel of the Flowerplate microtiter plate (48-well) of the BioLector cultivation system (m2plabs GmbH, Aachen, Germany). Methyl acetoacetate (MAA) was in each case added, in 0.1 ml, to the cell suspension to a final concentration of 40 mM. The Flowerplate microtiter plate was then incubated at 30° C., 1,200 rpm, shaking radius 3 mm, and the specific fluorescence was determined. The specific fluorescence obtained after 19 hours is shown in Table 1.

In addition, the alcohol dehydrogenase activity of the recombinant E. coli cells was determined in the individual batches. For this, the cells were harvested at 10.000×g, 4° C., 5 min and taken up in 100 mM potassium phosphate buffer, pH 6.5, 1 mM dithiothreitol, 1 mM $MgCl_2$. The cells were broken down by means of the Silamat S5 (Ivoclar Vivadent GmbH, Germany) with the aid of glass beads of 0.1 mm diameter. The crude extract which was obtained after centrifugation at 16.000×g, 4° C., 20 min was employed in the enzyme test for quantification of the alcohol dehydrogenase activity. The test contained 5 mM methyl acetoacetate, 0.25 mM NADPH and 1 mM $MgCl_2$ in 100 mM potassium phosphate buffer, pH 6.5, and 0.01-0.1 ml of crude extract. The reduction of NADP(H) was monitored at 340 nm and 30° C. An enzyme unit (U) is stated as that amount of crude extract which reduces 0.001 mmol of NADP(H) per minute. It is likewise given in Table 1.

Example 4

Isolation of Mutated Alcohol Dehydrogenase with Modified Substrate Recognition

The alcohol dehydrogenase Lbadh from Lactococcus lactis has a high activity with methyl acetoacetate, but only a low activity of about 10% with 4-methyl-2-pentanone as the substrate. In order to evolve an Lbadh with a higher activity, random mutations were inserted into pSenSox by error-prone PCR (epPCR). To insert the mutations, 10 ng of pSenSox were employed as the template per reaction, as well as 0.1-0.8 mM $Mn^{2+}$, at the lower concentrations of below <0.2 mM $Mn^{2+}$ a total concentration of at least 0.2 mM being established with $Mg^{2+}$, 0.5 µl of Taq polymerase from Fermentas (catalogue no. EP0401) was added per reaction. The polynucleotides SEQ. ID. No. 18:
ACAAGAATTCGCTAAGAGTGTCGGCACTCC SEQ. ID. No. 19:
GGCCAAGCTTCCGAAGAAGACACCATCAAG were used as primers. The reactions were incubated for 30 minutes. The reaction products were then treated with BamHI and SalI and ligated with the vector pSenSox likewise treated beforehand.

E. coli DH5αmer was transformed with the ligation products (Grant, 1990, Proceedings of the National Academy of Sciences, USA, 87, pages 4645-4649). After incubation for 30 h. transformants were washed off from the plates with 10 ml of 2×YT and diluted tenfold in fresh 2×YT medium. After incubation for 4 hours at 37° C., 20 mM 4-methyl-2-pentanone was added as the substrate, and after a further incubation for three hours the batches were sent for FACS analysis and sorting.

For FACS analysis and sorting of the cells with high fluorescence, the cell suspension in 2×YT medium was adjusted to an optical density of less than 0.1 and passed immediately to the FACS ARIA II high-speed cell sorter (Becton Dickinson GmbH, Tullastr. 8-12, 69126 Heidelberg). The analysis was carried out with the excitation wavelengths of 488 and 633 nm and the detection at the emission wavelengths of 530±15 nm and 660±10 nm under a sample pressure of 70 psi. The data were analysed with the software version BD DIVA 6.1.3 belonging to the apparatus. BD FACSflow was used as the sheath fluid. The electronic gating was set with the aid of the forward and backward scatter in order to exclude non-bacterial particles. In order to sort EYFP-positive cells, the next level of the electronic gating was selected, in order to exclude non-fluorescent cells. In this manner, 123 fluorescent cells were sorted out on Petri dishes which contained 2×YT medium.

Reaction vessels of the Flowerplate microtiter plate (48-well) of the BioLector cultivation system (m2plabs GmbH, Aachen, Germany) were inoculated, as described in Example 2, with the colonies obtained after incubation for 30 hours at 37° C. However, 20 mM 4-methyl-2-pentanone and not methyl acetoacetate was used as the substrate. After 120 minutes the specific fluorescence was quantified, and a clone was selected, the alcohol dehydrogenase activity of which was determined in the enzyme test as described in Example 3, 20 mM 4-methyl-2-pentanone was used as the substrate here.

The mutant with the plasmid pSen-A93M obtained in this way has a specific activity increased by 26% compared with the starting strain (Table 2), and a conversion rate with 4-methyl-2-pentanone as the substrate increased by 37%. The sequence of the plasmid pSen-A93M is deposited as SEQ. ID. No. 20.

TABLE 1

Correlation of the alcohol dehydrogenase activity of whole cells with the specific fluorescence.

| Strain | IPTG | Alcohol dehydrogenase activity (U mg$^{-1}$) | Specific fluorescence |
|---|---|---|---|
| BL21(DE3) pSennegK | − | 0.03 ± 0.01 | 0.06 |
| BL21(DE3) pSenSox, pET28a | − | 0.5 ± 0.1 | 0.09 |
| BL21(DE3) pSenL194S | − | 0.7 ± 0.3 | 0.11 |
| BL21(DE3) pSenL194A | − | 2.7 ± 0.6 | 0.17 |
| BL21(DE3) pSenSox | − | 6.2 ± 0.6 | 0.38 |
| BL21(DE3) pSenSox | + | 15.2 ± 2.0 | 0.45 |

TABLE 2

Increase in the activity and conversion rate of the alcohol dehydrogenase isolated by means of the NADP(H) nanosensor and FACS with 4-methyl-2-pentanone as the substrate.

| Strain | Alcohol dehydrogenase activity (U mg$^{-1}$) | $v_{max}$ (U mg$^{-1}$) | $K_M$ (mM) |
|---|---|---|---|
| DH5α pSensox | 1.9 ± 0.2 | 1.9 ± 0.02 | 0.10 ± 0.01 |
| DH5α pSenA93M | 2.4 ± 0.1 | 2.6 ± 0.03 | 0.88 ± 0.03 |

Example 5

Construction of the NADPH Nanosensor (Translational Fusion)

With the primer pairs SoxS_for_SphI_tl (SEQ. ID. No. 21) and SoxR_rev_SalI_tl (SEQ. ID. No. 22) and chromosomal DNA from *E. coli* DH5α as the template, the gene soxR was amplified together with the intergenic region of soxR-soxS and the first 63 nucleotides of soxS.

SoxS_for_SphI_tl:
ATCTGCATGCCGGCTGGTCAATATGCTCGTC

SoxR_rev_SalI_tl:
GCTAGTCGACCAAACTAAAGCGCCCTTGTG

With the primer pairs EYFP_for_SphI_tl (SEQ. ID. No. 23) and EYFP_rev_ClaI_tl (SEQ. ID. No. 24) and the vector pSenLys as the template, the gene eyfp was amplified. The vector pSenLys is described in the patent application WO-A-2011/138006.

EYFP_for_SphI_tl:
AGAGGCATGCGTGAGCAAGGGCGAGG

EYFP_rev_ClaI_tl:
GCGCATCGATTTATTACTTGTACAGCTCGTCATG

The vector pBtacLbadh codes for the NADPH-dependent alcohol dehydrogenase from *Lactobacillus brevis* (Lbadh). It is described in Ernst et al. (Ernst M, Kaup B. Müller M. Bringer-Meyer S, Sahm H, Appl. Microbiol. Biotechnol. 2005, 66(6), pages 629-34). The vector pBtacLbadh was treated with the restriction enzymes SalI and ClaI, and the vector fragment~5.0 kb in size was isolated from the agarose gel and treated with alkaline phosphatase and purified with the QIAquick Gel Extraction Kit (cat. no. 28704) from Quiagen (Hilden, Germany). The two PCR products and the vector were then ligated by means of T4 DNA ligase from New England BioLabs (New England Biolabs, 240 County Road, Ipswich, Mass. 01938-2723). The ligation batch was transformed directly into the *E. coli* strain DH5α. Selection of plasmid-carrying cells was carried out by plating out the transformation batch on LB agar (Sambrook et al.: "Molecular cloning: a laboratory manual", 2nd edition, Cold Spring Harbor Laboratory Press, Cold Spring Harbor, N.Y.), which had been supplemented with 50 mg/l of ampicillin. Plasmid DNA was isolated from a transformant and checked by treatment with the restriction enzyme BamHI with subsequent agarose gel electrophoresis. The plasmid was called pSenSox_tl and is deposited as the sequence SEQ. ID. No. 25.

The invention claimed is:

1. A cell comprising an NADPH(H) nanosensor, wherein the NADP(H) nanosensor comprises:
   i) a nucleic acid to which a regulator is capable of binding, wherein the oxidation state of the regulator depends on the cell's intra-cellular NADP(H) availability;
   ii) a promoter following the nucleic acid i), to which an RNA polymerase is capable of binding, wherein the affinity of the RNA polymerase for the promoter is influenced by the oxidation state of the regulator;
   iii) a nucleic acid which is under the control of the promoter ii) and which codes for an autofluorescent protein, wherein the autofluorescent protein is selected from the group consisting of green fluorescent protein (GFP), yellow fluorescent protein (YFP), blue fluorescent protein (BFP), cyan fluorescent protein (CFP), enhanced green fluorescent protein (EGFP), enhanced yellow fluorescent protein (EYFP), enhanced blue fluorescent protein (EBFP), enhanced cyan fluorescent protein (ECFP), DsRed, HcRed, AsRed, Am Cyan, ZsGreen, AcGFP and Zs Yellow, or a photoreceptor protein which contains a LOY domain,
      wherein components i) and ii) together have a nucleic acid sequence according to SEQ. ID. No. 01,
      wherein the NADP(H) nanosensor is present in the cell in the episomal form,
      wherein the cell, in addition to the NADP(H)-nanosensor, comprises a gene which codes for an NADP(H)-dependent enzyme that has been introduced into the cell, and
      wherein the cell is *Escherichia coli* (*E. coli*).

2. The cell according to claim 1, wherein the NADP(H) nanosensor comprises:
   (α1) the *E. coli* gene for SoxR (soxR);
   (α2) components i) and ii) downstream of (α1);
   (α3) at least the first 5 nucleotides of the soxS gene from *E. coli* following (α2);
   (α4) a nucleic acid which codes for an autofluorescent protein, following (α2) or (α3) and which is under the control of the soxS promoter, as component iii).

3. The cell according to claim 1, wherein the NADP(H) nanosensor comprises:
   (β1) the *E. coli* gene for SoxR (soxR);
   (β2) components i) and ii) downstream of (β1);
   (β3) the soxS gene from *E. coli* following (β2) and under the control of the soxS promoter or a part of this gene;
   (β3') a further nucleic acid following (β3) which at the mRNA level corresponds to a ribosome binding site;
   (β4) a nucleic acid, which codes for an autofluorescent protein, following (β3') and which is under the control of the soxS promoter, as component iii).

4. The cell according to claim 2 or 3, wherein component (α1) or (β1) is selected from the group consisting of:
   a) a nucleic acid sequence according to SEQ. ID. No. 02, and
   b) a nucleic acid sequence coding for a polypeptide with an amino acid sequence according to SEQ. ID. No. 03.

5. The cell according to claim 1, wherein the nucleic acid (iii) which codes for an auto fluorescent protein is the gene coding for enhanced yellow fluorescent protein (EYFP).

6. The cell according to claim 1, wherein the NADP(H) dependent enzyme is selected from the group consisting of alcohol dehydrogenases, aldehyde dehydrogenases, lactate dehydrogenases, enoate reductases, epoxide reductases, diaminopimelate dehydrogenases, amino acid dehydrogenases, aldehyde oxidoreductases, alkane reductases, amine reductases, epoxide dehydrogenases, carboxylic acid dehydrogenases, hydroxy acid ketoreductases and hydroxy acid dehalogenases.

* * * * *

```
                        SEQUENCE LISTING

<160> NUMBER OF SEQ ID NOS: 25

<210> SEQ ID NO 1
<211> LENGTH: 85
<212> TYPE: DNA
<213> ORGANISM: E. coli

<400> SEQUENCE: 1
aaatctgcct cttttcagtg ttcagttcgt taattcatct gttggggagt ataattcctc    60
aagttaactt gaggtaaagc gattt                                         85

<210> SEQ ID NO 2
<211> LENGTH: 465
<212> TYPE: DNA
<213> ORGANISM: E. coli

<400> SEQUENCE: 2
atggaaaaga aattaccccg cattaaagcg ctgctaaccc ccggcgaagt ggcgaaacgc    60
agcggtgtgg cggtatcggc gctgcatttc tatgaaagta aagggttgat taccagtatc   120
cgtaacagcg gcaatcagcg gcgatataaa cgtgatgtgt tgcgatatgt tgcaattatc   180
```

```
aaaattgctc agcgtattgg cattccgctg gcgaccattg gtgaagcgtt tggcgtgttg   240
cccgaagggc atacgttaag tgcgaaagag tggaaacagc tttcgtccca atggcgagaa   300
gagttggatc ggcgcattca taccttagtg gcgctgcgtg acgaactgga cggatgtatt   360
ggttgtggct gcctttcgcg cagtgattgc ccgttgcgta acccgggcga ccgcttagga   420
gaagaaggta ccggcgcacg cttgctggaa gatgaacaaa actaa             465
```

<210> SEQ ID NO 3
<211> LENGTH: 154
<212> TYPE: PRT
<213> ORGANISM: E. coli
<400> SEQUENCE: 3

```
Met Glu Lys Lys Leu Pro Arg Ile Lys Ala Leu Leu Thr Pro Gly Glu
1               5                   10                  15

Val Ala Lys Arg Ser Gly Val Ala Val Ser Ala Leu His Phe Tyr Glu
                20                  25                  30

Ser Lys Gly Leu Ile Thr Ser Ile Arg Asn Ser Gly Asn Gln Arg Arg
            35                  40                  45

Tyr Lys Arg Asp Val Leu Arg Tyr Val Ala Ile Ile Lys Ile Ala Gln
50                  55                  60

Arg Ile Gly Ile Pro Leu Ala Thr Ile Gly Glu Ala Phe Gly Val Leu
65                  70                  75                  80

Pro Glu Gly His Thr Leu Ser Ala Lys Glu Trp Lys Gln Leu Ser Ser
                85                  90                  95

Gln Trp Arg Glu Glu Leu Asp Arg Arg Ile His Thr Leu Val Ala Leu
                100                 105                 110

Arg Asp Glu Leu Asp Gly Cys Ile Gly Cys Gly Cys Leu Ser Arg Ser
            115                 120                 125

Asp Cys Pro Leu Arg Asn Pro Gly Asp Arg Leu Gly Glu Glu Gly Thr
130                 135                 140

Gly Ala Arg Leu Leu Glu Asp Glu Gln Asn
145                 150
```

<210> SEQ ID NO 4
<211> LENGTH: 34
<212> TYPE: DNA
<213> ORGANISM: Artificial Sequence
<220> FEATURE:
<223> OTHER INFORMATION: SoxS_for_SphI
<400> SEQUENCE: 4

```
atctgcatgc ttacggctgg tcaatatgct cgtc                              34
```

<210> SEQ ID NO 5
<211> LENGTH: 30
<212> TYPE: DNA
<213> ORGANISM: Artificial Sequence
<220> FEATURE:
<223> OTHER INFORMATION: SoxR_rev_SalI
<400> SEQUENCE: 5

```
gctagtcgac caaactaaag cgcccttgtg                                   30
```

<210> SEQ ID NO 6
<211> LENGTH: 41
<212> TYPE: DNA
<213> ORGANISM: Artificial Sequence
<220> FEATURE:
<223> OTHER INFORMATION: EYFP_for_SphI

<400> SEQUENCE: 6
agaggcatgc aaggagaatt acatggtgag caagggcgag g          41

<210> SEQ ID NO 7
<211> LENGTH: 35
<212> TYPE: DNA
<213> ORGANISM: Artificial Sequence
<220> FEATURE:
<223> OTHER INFORMATION: EYFP_rev_ClaI

<400> SEQUENCE: 7
gcgcatcgat ttattacttg tacagctcgt ccatg                 35

<210> SEQ ID NO 8
<211> LENGTH: 6436
<212> TYPE: DNA
<213> ORGANISM: Artificial Sequenz
<220> FEATURE:
<223> OTHER INFORMATION: pSenSox

<400> SEQUENCE: 8
ttcatgtcta accgtttgga tggtaaggta gcaatcatta caggtggtac gttgggtatc    60
ggtttagcta tcgccacgaa gttcgttgaa gaaggggcta aggtcatgat taccggccgg   120
cacagcgatt ttggtgaaaa agcagctaag agtgtcggca ctcctgatca gattcaattt   180
ttccaacatg attcttccga tgaagacggc tggacgaaat tattcgatgc aacggaaaaa   240
gcctttggcc cagtttctac attagttaat aacgctggga tcgcggttaa caagagtgtc   300
gaagaaacca cgactgctga atggcgtaaa ttattagccg tcaaccttga tggtgtcttc   360
ttcggtaccc gattagggat tcaacggatg aagaacaaag cttaggggc ttccatcatc   420
aacatgtctt cgatcgaagg cttgtgggt gatcctagct tagggcttta caacgcatct   480
aaaggggccg tacggattat gtccaagtca gctgccttag attgtgccct aaaggactac   540
gatgttcggg taaacactgt tcaccctggc tacatcaaga caccattggt tgatgaccta   600
ccaggggccg aagaagcgat gtcacaacgg accaagacgc caatgggcca tatcggtgaa   660
cctaacgata ttgcctacat ctgtgtttac ttggcttcta cgaatctaa atttgcaacg   720
ggttctgaat tgtagttga cggtggctac actgctcaat agtaagcttc tgttttggcg   780
gatgagagaa gattttcagc ctgatacaga ttaaatcaga acgcagaagc ggtctgataa   840
aacagaattt gcctggcggc agtagcgcgg tggtcccacc tgaccccatg ccgaactcag   900
aagtgaaacg ccgtagcgcc gatggtagtg tggggtctcc ccatgcgaga gtagggaact   960
gccaggcatc aaataaaacg aaaggctcag tcgaaagact gggcctttcg ttttatctgt  1020
tgtttgtcgg tgaacgctct cctgagtagg acaaatccgc cgggagcgga tttgaacgtt  1080
gcgaagcaac ggcccggagg gtggcgggca ggacgcccgc cataaactgc caggcatcaa  1140
attaagcaga aggccatcct gacgatggc cttttgcgt ttctacaaac tctttttgttt  1200
attttctaa atacattcaa atatgtatcc gctcatgaga caataaccct gataaatgct  1260
tcaataatat tgaaaagga agagtatgag tattcaacat ttccgtgtcg cccttattcc  1320
cttttttgcg gcattttgcc ttcctgtttt tgctcaccca gaaacgctgg tgaaagtaaa  1380
agatgctgaa gatcagttgg gtgcacgagt gggttacatc gaactggatc tcaacagcgg  1440
taagatccct gagagtttc gccccgaaga acgttttcca atgatgagca cttttaaagt  1500
tctgctatgt ggcgcggtat tatcccgtgt tgacgccggg caagagcaac tcggtcgccg  1560

```
catacactat tctcagaatg acttggttga gtactcacca gtcacagaaa agcatcttac    1620
ggatggcatg acagtaagag aattatgcag tgctgccata accatgagtg ataacactgc    1680
ggccaactta cttctgacaa cgatcggagg accgaaggag ctaaccgctt ttttgcacaa    1740
catgggggat catgtaactc gccttgatcg ttgggaaccg gagctgaatg aagccatacc    1800
aaacgacgag cgtgacacca cgatgcctgt agcaatggca acaacgttgc gcaaactatt    1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg gtctcgcgg tatcattgca gcactgggc cagatggtaa    2040 gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatccttttt ttctgcgcgt    2340
aatctgctgc ttgcaaacaa aaaaaccacc gctaccagcg gtggtttgtt tgccggatca    2400
agagctacca actcttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata gtcgtgtct    2580 taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880 gtcaggggg cggagcctat ggaaaaacgc cagcaacgcg gcctttttac ggttcctggc    2940
cttttgctgg ccttttgctc acatgttctt tcctgcgtta tcccctgatt ctgtggataa    3000
ccgtattacc gcctttgagt gagctgatac cgctcgccgc agccgaacga ccgagcgcag    3060
cgagtcagtg agcgaggaag cggaagagcg cctgatgcgg tattttctcc ttacgcatct    3120
gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
caagctgtga ccgtctccgg gagctgcatg tgtcagaggt tttcaccgtc atcaccgaaa    3360
cgcgcgaggc agctgcggta agctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag gcggtttttt cctgtttggt cacttgatg cctccgtgta    3540 agggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
```

```
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
tagcgaggtg ccgccggctt ccattcaggt cgaggtggcc cggctccatg caccgcgacg    4200
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg aagcgagaa gaatcataat    4440 ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
gaaggcttga gcgagggcgt gcaagattcc gaataccgca agcgacaggc cgatcatcgt    4620
cgcgctccag cgaaagcggt cctcgccgaa aatgacccag agcgctgccg gcacctgtcc    4680
tacgagttgc atgataaaga agacagtcat aagtgcggcg acgatagtca tgccccgcgc    4740
ccaccggaag gagctgactg ggttgaaggc tctcaagggc atcggtcgac caaactaaag    4800 cgccttgtg gcgctttagt tttgttcatc ttccagcaag cgtgcgccgg taccttcttc    4860
tcctaagcgg tcgcccgggt tacgcaacgg gcaatcactg cgcgaaaggc agccacaacc    4920
aatacatccg tccagttcgt cacgcagcgc cactaaggta tgaatgcgcc gatccaactc    4980
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaacccctt tactttcata gaaatgcagc gccgataccg ccacaccgct    5220
gcgtttcgcc acttcgccgg gggttagcag cgctttaatg cggggtaatt tcttttccat    5280
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
cttcggctac ggcctgcagt gcttcgcccg ctaccccgac cacatgaagc agcacgactt    5700
cttcaagtcc gccatgcccg aaggctacgt ccaggagcgc accatcttct tcaaggacga    5760
cggcaactac aagacccgcg ccgaggtgaa gttcgagggc gacaccctgg tgaaccgcat    5820
cgagctgaag ggcatcaact tcaaggagga cggcaacatc ctggggcaca agctggagta    5880
caactacaac agccacaacg tctatatcat ggccgacaag cagaagaacg gcatcaaggt    5940
gaacttcaag atccgccaca acatcgaggg cggcagcgtg cagctcgccg accactacca    6000
gcagaacacc cccatcggcg acggccccgt gctgctgccc gacaaccact acctgagcta    6060
ccagtccgcc ctgagcaaag accccaacga gaagcgcgat cacatggtcc tgctggagtt    6120
cgtgaccgcc gccgggatca ctctcggcat ggacgagctg tacaagtaat aaatcgatcc    6180
ggagcttatc gactgcacgg tgcaccaatg cttctggcgt caggcagcca tcggaagctg    6240
tggtatggct gtgcaggtcg taaatcactg cataattcgt gtcgctcaag gcgcactccc    6300
```

```
gttctggata atgttttttg cgccgacatc ataacggttc tggcaaatat tctgaaatga    6360
gctgttgaca attaatcatc ggctcgtata atgtgtggaa ttgtgagcgg ataacaattt    6420
cacacaggaa acagaa                                                    6436

<210> SEQ ID NO 9
<211> LENGTH: 30
<212> TYPE: DNA
<213> ORGANISM: Artificial Sequence
<220> FEATURE:
<223> OTHER INFORMATION: ADH_negK_for

<400> SEQUENCE: 9
acaagaattc gctaagagtg tcggcactcc                                       30

<210> SEQ ID NO 10
<211> LENGTH: 30
<212> TYPE: DNA
<213> ORGANISM: Artificial Sequence
<220> FEATURE:
<223> OTHER INFORMATION: ADH_negK_rev

<400> SEQUENCE: 10
ggccaagctt ccgaagaaga caccatcaag                                       30

<210> SEQ ID NO 11
<211> LENGTH: 5897
<212> TYPE: DNA
<213> ORGANISM: Artificial Sequence
<220> FEATURE:
<223> OTHER INFORMATION: vector

<400> SEQUENCE: 11
agcttctgtt ttggcggatg agagaagatt ttcagcctga tacagattaa atcagaacgc      60
agaagcggtc tgataaaaca gaatttgcct ggcggcagta gcgcggtggt cccacctgac     120
cccatgccga actcagaagt gaaacgccgt agcgccgatg gtagtgtggg gtctccccat     180
gcgagagtag ggaactgcca ggcatcaaat aaaacgaaag gctcagtcga agactgggc     240 ctttcgtttt atctgttgtt tgtcggtgaa cgctctcctg agtaggacaa atccgccggg     300
agcggatttg aacgttgcga agcaacggcc cggagggtgg cgggcaggac gcccgccata     360
aactgccagg catcaaatta agcagaaggc catcctgacg gatggccttt ttgcgtttct     420
acaaactctt tgtttatttt tctaaatac attcaaatat gtatccgctc atgagacaat     480
aaccctgata aatgcttcaa taatattgaa aaaggaagag tatgagtatt caacatttcc     540
gtgtcgccct tattcccttt tttgcggcat tttgccttcc tgttttgct cacccagaaa     600 cgctggtgaa agtaaaagat gctgaagatc agttgggtgc acgagtgggt tacatcgaac     660
tggatctcaa cagcggtaag atccttgaga gttttcgccc cgaagaacgt tttccaatga     720
tgagcacttt taaagttctg ctatgtggcg cggtattatc ccgtgttgac gccgggcaag     780
agcaactcgg tcgccgcata cactattctc agaatgactt ggttgagtac tcaccagtca     840
cagaaaagca tcttacggat ggcatgacag taagagaatt atgcagtgct gccataacca     900
tgagtgataa cactgcggcc aacttacttc tgacaacgat cggaggaccg aaggagctaa     960 ccgcttttt gcacaacatg gggatcatg taactcgcct tgatcgttgg gaaccggagc    1020
tgaatgaagc cataccaaac gacgagcgtg acaccacgat gcctgtagca atggcaacaa    1080
cgttgcgcaa actattaact ggcgaactac ttactctagc ttcccggcaa caattaatag    1140
actggatgga ggcggataaa gttgcaggac cacttctgcg ctcggccctt ccggctggct    1200
```

```
ggtttattgc tgataaatct ggagccggtg agcgtgggtc tcgcggtatc attgcagcac    1260
tggggccaga tggtaagccc tcccgtatcg tagttatcta cacgacgggg agtcaggcaa    1320
ctatggatga acgaaataga cagatcgctg agataggtgc ctcactgatt aagcattggt    1380
aactgtcaga ccaagtttac tcatatatac tttagattga tttaaaactt cattttaat    1440 ttaaaaggat ctaggtgaag atccttttg ataatctcat gaccaaaatc ccttaacgtg    1500
agttttcgtt ccactgagcg tcagaccccg tagaaaagat caaggatctc tcttgagatc    1560
ctttttttct gcgcgtaatc tgctgcttgc aaacaaaaaa accaccgcta ccagcggtgg    1620
tttgtttgcc ggatcaagag ctaccaactc tttttccgaa ggtaactggc ttcagcagag    1680
cgcagatacc aaatactgtc cttctagtgt agccgtagtt aggccaccac ttcaagaact    1740
ctgtagcacc gcctacatac ctcgctctgc taatcctgtt accagtggct gctgccagtg    1800
gcgataagtc gtgtcttacc gggttggact caagacgata gttaccggat aaggcgcagc    1860
ggtcgggctg aacggggggt tcgtgcacac agcccagctt ggagcgaacg acctacaccg    1920
aactgagata cctacagcgt gagctatgag aaagcgccac gcttcccgaa gggagaaagg    1980
cggacaggta tccggtaagc ggcagggtcg aacaggaga gcgcacgagg gagcttccag    2040
ggggaaacgc ctggtatctt tatagtcctg tcgggtttcg ccacctctga cttgagcgtc    2100
gatttttgtg atgctcgtca ggggggcgga gcctatggaa aaacgccagc aacgcggcct    2160
ttttacggtt cctggccttt tgctggcctt ttgctcacat gttctttcct gcgttatccc    2220
ctgattctgt ggataaccgt attaccgcct ttgagtgagc tgataccgct cgccgcagcc    2280
gaacgaccga gcgcagcgag tcagtgagcg aggaagcgga agagcgcctg atgcggtatt    2340
ttctccttac gcatctgtgc ggtatttcac accgcatatg gtgcactctc agtacaatct    2400
gctctgatgc cgcatagtta agccagtata cactccgcta tcgctacgtg actgggtcat    2460
ggctgcgccc cgacacccgc caacacccgc tgacgcgccc tgacgggctt gtctgctccc    2520
ggcatccgct tacagacaag ctgtgaccgt ctccgggagc tgcatgtgtc agaggttttc    2580
accgtcatca ccgaaacgcg cgaggcagct gcggtaaagc tcatcagcgt ggtcgtgaag    2640
cgattcacag atgtctgcct gttcatccgc gtccagctcg ttgagtttct ccagaagcgt    2700
taatgtctgg cttctgataa agcgggccat gttaagggcg ttttttcct gtttggtcac    2760 ttgatgcctc cgtgtaaggg ggaatttctg ttcatggggg taatgatacc gatgaaacga    2820
gagaggatgc tcacgatacg ggttactgat gatgaacatg cccggttact ggaacgttgt    2880
gagggtaaac aactggcggt atggatgcgg cgggaccaga gaaaaatcac tcagggtcaa    2940
tgccagcgct tcgttaatac agatgtaggt gttccacagg gtagccagca gcatcctgcg    3000
atgcagatcc ggaacataat ggtgcagggc gctgacttcc gcgtttccag actttacgaa    3060
acacggaaac cgaagaccat tcatgttgtt gctcaggtcg cagacgtttt gcagcagcag    3120
tcgcttcacg ttcgctcgcg tatcggtgat tcattctgct aaccagtaag caacccgc    3180 cagcctagcc gggtcctcaa cgacaggagc acgatcatgc gcacccgtgg ccaggaccca    3240
acgctgcccg agatgcgccg cgtgcggctg ctggagatgg cggacgcgat ggatatgttc    3300
tgccaagggt tggtttgcgc attcacagtt ctccgcaaga attgattggc tccaattctt    3360
ggagtggtga atccgttagc gaggtgccgc cggcttccat tcaggtcgag gtggcccggc    3420
tccatgcacc gcgacgcaac gcggggaggc agacaaggta tagggcggcg cctacaatcc    3480
atgccaaccc gttccatgtg ctcgccgagg cggcataaat cgccgtgacg atcagcggtc    3540
```

```
cagtgatcga agttaggctg gtaagagccg cgagcgatcc ttgaagctgt ccctgatggt    3600
cgtcatctac ctgcctggac agcatggcct gcaacgcggg catcccgatg ccgccggaag    3660
cgagaagaat cataatgggg aaggccatcc agcctcgcgt cgcgaacgcc agcaagacgt    3720
agcccagcgc gtcggccgcc atgccggcga taatggcctg cttctcgccg aaacgtttgg    3780
tggcgggacc agtgacgaag gcttgagcga gggcgtgcaa gattccgaat accgcaagcg    3840
acaggccgat catcgtcgcg ctccagcgaa agcggtcctc gccgaaaatg acccagagcg    3900
ctgccggcac ctgtcctacg agttgcatga taaagaagac agtcataagt gcggcgacga    3960
tagtcatgcc ccgcgcccac cggaaggagc tgactgggtt gaaggctctc aagggcatcg    4020
gtcgaccaaa ctaaagcgcc cttgtggcgc tttagttttg ttcatcttcc agcaagcgtg    4080
cgccggtacc ttcttctcct aagcggtcgc ccggggttacg caacgggcaa tcactgcgcg    4140
aaaggcagcc acaaccaata catccgtcca gttcgtcacg cagcgccact aaggtatgaa    4200
tgcgccgatc caactcttct cgccattggg acgaaagctg tttccactct ttcgcactta    4260
acgtatgccc ttcgggcaac acgccaaacg cttcaccaat ggtcgccagc ggaatgccaa    4320
tacgctgagc aattttgata attgcaacat atcgcaacac atcacgttta tatcgccgct    4380
gattgccgct gttacggata ctggtaatca acccttact ttcatagaaa tgcagcgccg    4440
ataccgccac accgctgcgt ttcgccactt cgccggggt tagcagcgct ttaatgcggg    4500
gtaatttctt ttccataaat cgctttacct caagttaact tgaggaatta tactccccaa    4560
cagatgaatt aacgaactga acactgaaaa gaggcagatt tatgtcccat cagaaaatta    4620
ttcaggatct tatcgcatgg attgacgagc atattgacca gccgtaagca tgcaaggaga    4680
attacatggt gagcaagggc gaggagctgt tcaccggggt ggtgcccatc ctggtcgagc    4740
tggacgcga cgtaaacggc cacaagttca gcgtgtccgg cgagggcgag ggcgatgcca    4800
cctacggcaa gctgaccctg aagttcatct gcaccaccgg caagctgccc gtgccctggc    4860
ccacccctcgt gaccaccttc ggctacggcc tgcagtgctt cgcccgctac cccgaccaca    4920
tgaagcagca cgacttcttc aagtccgcca tgcccgaagg ctacgtccag gagcgcacca    4980
tcttcttcaa ggacgacggc aactacaaga cccgcgccga ggtgaagttc gagggcgaca    5040
cccctggtgaa ccgcatcgag ctgaagggca tcaacttcaa ggaggacggc aacatcctgg    5100
ggcacaagct ggagtacaac tacaacagcc acaacgtcta tatcatggcc gacaagcaga    5160
agaacggcat caaggtgaac ttcaagatcc gccacaacat cgagggcggc agcgtgcagc    5220
tcgccgacca ctaccagcag aacacccccca tcggcgacgg ccccgtgctg ctgcccgaca    5280
accactacct gagctaccag tccgccctga gcaaagaccc caacgagaag cgcgatcaca    5340
tggtcctgct ggagttcgtg accgccgccg ggatcactct cggcatggac gagctgtaca    5400
agtaataaat cgatccggag cttatcgact gcacggtgca ccaatgcttc tggcgtcagg    5460
cagccatcgg aagctgtggt atggctgtgc aggtcgtaaa tcactgcata attcgtgtcg    5520
ctcaaggcgc actcccgttc tggataatgt ttttgcgcc gacatcataa cggttctggc    5580
aaatattctg aaatgagctg ttgacaatta atcatcggct cgtataatgt gtggaattgt    5640
gagcggataa caatttcaca caggaaacag aattcgctaa gagtgtcggc actcctgatc    5700
agattcaatt tttccaacat gattcttccg atgaagacgg ctggacgaaa ttattcgatg    5760
caacggaaaa agcctttggc ccagtttcta cattagttaa taacgctggg atcgcggtta    5820
acaagagtgt cgaagaaacc acgactgctg aatggcgtaa attattagcc gtcaaccttg    5880
atggtgtctt cttcgga                                                   5897
```

<210> SEQ ID NO 12
<211> LENGTH: 30
<212> TYPE: DNA
<213> ORGANISM: Artificial Sequence
<220> FEATURE:
<223> OTHER INFORMATION: L194S_for

<400> SEQUENCE: 12
ctggctacat caagacacca tctgttgatg                                     30

<210> SEQ ID NO 13
<211> LENGTH: 30
<212> TYPE: DNA
<213> ORGANISM: Artificial Sequence
<220> FEATURE:
<223> OTHER INFORMATION: L194S_rev

<400> SEQUENCE: 13
cggcccctgg taggtcatca acagatggtg                                     30

<210> SEQ ID NO 14
<211> LENGTH: 6436
<212> TYPE: DNA
<213> ORGANISM: Artificial Sequence
<220> FEATURE:
<223> OTHER INFORMATION: vector

<400> SEQUENCE: 14
ttcatgtcta accgtttgga tggtaaggta gcaatcatta caggtggtac gttgggtatc      60
ggtttagcta tcgccacgaa gttcgttgaa gaaggggcta aggtcatgat taccggccgg     120
cacagcgatg ttggtgaaaa agcagctaag agtgtcggca ctcctgatca gattcaattt     180
ttccaacatg attcttccga tgaagacggc tggacgaaat tattcgatgc aacggaaaaa     240
gcctttggcc cagttttcta cattagttaat aacgctggga tcgcggttaa caagagtgtc     300
gaagaaacca cgactgctga atggcgtaaa ttattagccg tcaaccttga tggtgtcttc     360
ttcggtaccc gattagggat tcaacgatg aagaacaaag cttaggggc ttccatcatc      420
aacatgtctt cgatcgaagg ctttgtgggt gatcctagct taggggctta caacgcatct     480
aaagggccg tacggattat gtccaagtca gctgccttag attgtgccct aaaggactac     540
gatgttcggg taaacactgt tcaccctggc tacatcaaga caccatctgt tgatgaccta     600
ccaggggccg aagaagcgat gtcacaacgg accaagacgc caatgggcca tatcggtgaa     660
cctaacgata ttgcctacat ctgtgtttac ttggcttcta cgaatctaaa atttgcaacg     720
ggttctgaat ttgtagttga cggtggctac actgctcaat agtaagcttc tgttttggcg     780
gatgagagaa gattttcagc ctgatacaga ttaaatcaga acgcagaagc ggtctgataa     840
aacagaattt gcctggcggc agtagcgcgg tggtcccacc tgaccccatg ccgaactcag     900
aagtgaaacg ccgtagcgcc gatggtagtg tggggtctcc ccatgcgaga gtagggaact     960
gccaggcatc aaataaaacg aaaggctcag tcgaaagact gggcctttcg ttttatctgt    1020
tgtttgtcgg tgaacgctct cctgagtagg acaaatccgc cgggagcgga tttgaacgtt    1080
gcgaagcaac ggcccggagg gtggcgggca ggacgcccgc cataaactgc caggcatcaa    1140
attaagcaga aggccatcct gacggatggc cttttttgcgt ttctacaaac tcttttgttt    1200
attttttctaa atacattcaa atatgtatcc gctcatgaga caataaccct gataaatgct    1260
tcaataatat tgaaaaagga agagtatgag tattcaacat ttccgtgtcg cccttattcc    1320

```
cttttttgcg gcattttgcc ttcctgtttt tgctcaccca gaaacgctgg tgaaagtaaa    1380
agatgctgaa gatcagttgg gtgcacgagt gggttacatc gaactggatc tcaacagcgg    1440
taagatcctt gagagttttc gccccgaaga acgttttcca atgatgagca cttttaaagt    1500
tctgctatgt ggcgcggtat tatcccgtgt tgacgccggg caagagcaac tcggtcgccg    1560
catacactat tctcagaatg acttggttga gtactcacca gtcacagaaa agcatcttac    1620
ggatggcatg acagtaagag aattatgcag tgctgccata accatgagtg ataacactgc    1680
ggccaactta cttctgacaa cgatcggagg accgaaggag ctaaccgctt ttttgcacaa    1740
catgggggat catgtaactc gccttgatcg ttgggaaccg gagctgaatg aagccatacc    1800
aaacgacgag cgtgacacca cgatgcctgt agcaatggca acaacgttgc gcaaactatt    1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg ggtctcgcgg tatcattgca gcactggggc cagatggtaa    2040
gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatcctttt ttctgcgcgt    2340 aatctgctgc ttgcaaacaa aaaaaccacc gctaccagcg gtggtttgtt tgccggatca    2400
agagctacca actcttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880 gtcaggggg cggagcctat ggaaaaacgc cagcaacgcg gcctttttac ggttcctggc    2940
cttttgctgg ccttttgctc acatgttctt tcctgcgtta tcccctgatt ctgtggataa    3000
ccgtattacc gcctttgagt gagctgatac cgctcgccgc agccgaacga ccagcgcag    3060 cgagtcagtg agcgaggaag cggaagagcg cctgatgcgg tattttctcc ttacgcatct    3120
gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
caagctgtga ccgtctccgg gagctgcatg tgtcagaggt tttcaccgtc atcaccgaaa    3360
cgcgcgaggc agctgcggta aagctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag gcggttttt tcctgtttgg tcacttgatg cctccgtgta    3540
agggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
```

```
atacagatgt aggtgttcca cagggtagcc agcagcatcc tgcgatgcag atccggaaca   3780
taatggtgca gggcgctgac ttccgcgttt ccagacttta cgaaacacgg aaaccgaaga   3840
ccattcatgt tgttgctcag gtcgcagacg ttttgcagca gcagtcgctt cacgttcgct   3900
cgcgtatcgt tgattcattc tgctaaccag taaggcaacc ccgccagcct agccgggtcc   3960
tcaacgacag gagcacgatc atgcgcaccc gtggccagga cccaacgctg cccgagatgc   4020
gccgcgtgcg gctgctggag atggcggacg cgatggatat gttctgccaa gggttggttt   4080
gcgcattcac agttctccgc aagaattgat tggctccaat tcttggagtg gtgaatccgt   4140
tagcgaggtg ccgccggctt ccattcaggt cgaggtggcc cggctccatg caccgcgacg   4200
caacgcgggg aggcagacaa ggtatagggc ggcgcctaca atccatgcca acccgttcca   4260
tgtgctcgcc gaggcggcat aaatcgccgt gacgatcagc ggtccagtga tcgaagttag   4320
gctggtaaga gccgcgagcg atccttgaag ctgtccctga tggtcgtcat ctacctgcct   4380
ggacagcatg gcctgcaacg cgggcatccc gatgccgccg aagcgagaa gaatcataat   4440 ggggaaggcc atccagcctc gcgtcgcgaa cgccagcaag acgtagccca gcgcgtcggc   4500
cgccatgccg gcgataatgg cctgcttctc gccgaaacgt ttggtggcgg gaccagtgac   4560
gaaggcttga gcgagggcgt gcaagattcc gaataccgca agcgacaggc cgatcatcgt   4620
cgcgctccag cgaaagcggt cctcgccgaa aatgacccag agcgctgccg gcacctgtcc   4680
tacgagttgc atgataaaga agacagtcat aagtgcggcg acgatagtca tgccccgcgc   4740
ccaccggaag gagctgactg ggttgaaggc tctcaagggc atcggtcgac caaactaaag   4800
cgcccttgtg gcgctttagt tttgttcatc ttccagcaag cgtgcgccgg taccttcttc   4860
tcctaagcgg tcgcccgggt tacgcaacgg gcaatcactg cgcgaaaggc agccacaacc   4920
aatacatccg tccagttcgt cacgcagcgc cactaaggta tgaatgcgcc gatccaactc   4980
ttctcgccat tgggacgaaa gctgttttcca ctctttcgca cttaacgtat gcccttcggg   5040
caacacgcca aacgcttcac caatggtcgc cagcggaatg ccaatacgct gagcaatttt   5100
gataattgca acatatcgca acacatcacg tttatatcgc cgctgattgc cgctgttacg   5160
gatactggta atcaaccctt tactttcata gaaatgcagc gccgataccg ccacaccgct   5220
gcgtttcgcc acttcgccgg gggttagcag cgctttaatg cggggtaatt tcttttccat   5280
aaatcgcttt acctcaagtt aacttgagga attatactcc ccaacagatg aattaacgaa   5340
ctgaacactg aaaagaggca gatttatgtc ccatcagaaa attattcagg atcttatcgc   5400
atggattgac gagcatattg accagccgta agcatgcaag gagaattaca tggtgagcaa   5460
gggcgaggag ctgttcaccg gggtggtgcc catcctggtc gagctggacg gcgacgtaaa   5520
cggccacaag ttcagcgtgt ccggcgaggg cgagggcgat gccacctacg gcaagctgac   5580
cctgaagttc atctgcacca ccggcaagct gcccgtgccc tggcccaccc tcgtgaccac   5640
cttcggctac ggcctgcagt gcttcgcccg ctaccccgac cacatgaagc agcacgactt   5700
cttcaagtcc gccatgcccg aaggctacgt ccaggagcgc accatcttct tcaaggacga   5760
cggcaactac aagacccgcg ccgaggtgaa gttcgagggc gacaccctgg tgaaccgcat   5820
cgagctgaag ggcatcaact tcaaggagga cggcaacatc ctggggcaca agctggagta   5880
caactacaac agccacaacg tctatatcat ggccgacaag cagaagaacg gcatcaaggt   5940
gaacttcaag atccgccaca acatcgaggg cggcagcgtg cagctcgccg accactacca   6000
gcagaacacc cccatcggcg acggccccgt gctgctgccc gacaaccact acctgagcta   6060
```

```
ccagtccgcc ctgagcaaag accccaacga gaagcgcgat cacatggtcc tgctggagtt      6120
cgtgaccgcc gccgggatca ctctcggcat ggacgagctg tacaagtaat aaatcgatcc      6180
ggagcttatc gactgcacgg tgcaccaatg cttctggcgt caggcagcca tcggaagctg      6240
tggtatggct gtgcaggtcg taaatcactg cataattcgt gtcgctcaag gcgcactccc      6300
gttctggata atgttttttg cgccgacatc ataacggttc tggcaaatat tctgaaatga      6360
gctgttgaca attaatcatc ggctcgtata atgtgtggaa ttgtgagcgg ataacaattt      6420
cacacaggaa acagaa                                                     6436

<210> SEQ ID NO 15
<211> LENGTH: 30
<212> TYPE: DNA
<213> ORGANISM: Artificial Sequence
<220> FEATURE:
<223> OTHER INFORMATION: L194A_for

<400> SEQUENCE: 15
ctggctacat caagacacca gcggttgatg                                        30

<210> SEQ ID NO 16
<211> LENGTH: 30
<212> TYPE: DNA
<213> ORGANISM: Artificial Sequence
<220> FEATURE:
<223> OTHER INFORMATION: L194A_rev

<400> SEQUENCE: 16
cggcccctgg taggtcatca accgctggtg                                        30

<210> SEQ ID NO 17
<211> LENGTH: 6436
<212> TYPE: DNA
<213> ORGANISM: Artificial Sequence
<220> FEATURE:
<223> OTHER INFORMATION: vector

<400> SEQUENCE: 17
ttcatgtcta accgtttgga tggtaaggta gcaatcatta caggtggtac gttgggtatc        60
ggtttagcta tcgccacgaa gttcgttgaa gaaggggcta aggtcatgat taccggccgg      120
cacagcgatg ttggtgaaaa agcagctaag agtgtcggca ctcctgatca gattcaattt      180
ttccaacatg attcttccga tgaagacggc tggacgaaat tattcgatgc aacggaaaaa      240
gcctttggcc cagtttctac attagttaat aacgctggga tcgcggttaa caagagtgtc      300
gaagaaacca cgactgctga atggcgtaaa ttattagccg tcaaccttga tggtgtcttc      360
ttcggtaccc gattagggat tcaacgatg aagaacaaag cttaggggc ttccatcatc      420 aacatgtctt cgatcgaagg ctttgtgggt gatcctagct taggggctta caacgcatct      480
aaaggggccg tacggattat gtccaagtca gctgccttag attgtgccct aaaggactac      540
gatgttcggg taaacactgt tcaccctggc tacatcaaga caccagcggt tgatgaccta      600
ccaggggccg aagaagcgat gtcacaacgg accaagacgc caatgggcca tcggtgaa      660 cctaacgata ttgcctacat ctgtgtttac ttggcttcta acgaatctaa atttgcaacg      720
ggttctgaat ttgtagttga cggtggctac actgctcaat agtaagcttc tgttttggcg      780
gatgagagaa gattttcagc ctgatacaga ttaaatcaga acgcagaagc ggtctgataa      840
aacagaattt gcctggcggc agtagcgcgg tggtcccacc tgaccccatg ccgaactcag      900
aagtgaaacg ccgtagcgcc gatggtagtg tggggtctcc ccatgcgaga gtagggaact      960
```

```
gccaggcatc aaataaaacg aaaggctcag tcgaaagact gggcctttcg ttttatctgt    1020
tgtttgtcgg tgaacgctct cctgagtagg acaaatccgc cgggagcgga tttgaacgtt    1080
gcgaagcaac ggcccggagg gtggcgggca ggacgcccgc cataaactgc caggcatcaa    1140
attaagcaga aggccatcct gacgatggc cttttttgcgt ttctacaaac tcttttgttt    1200 attttttctaa atacattcaa atatgtatcc gctcatgaga caataaccct gataaatgct    1260
tcaataatat tgaaaaagga agagtatgag tattcaacat ttccgtgtcg cccttattcc    1320
cttttttgcg catttttgcc ttcctgtttt tgctcaccca gaaacgctgg tgaaagtaaa    1380
agatgctgaa gatcagttgg gtgcacgagt gggttacatc gaactggatc tcaacagcgg    1440
taagatcctt gagagttttc gccccgaaga acgttttcca atgatgagca cttttaaagt    1500
tctgctatgt ggcgcggtat tatcccgtgt tgacgccggg caagagcaac tcggtcgccg    1560
catacactat tctcagaatg acttggttga gtactcacca gtcacagaaa agcatcttac    1620
ggatggcatg acagtaagag aattatgcag tgctgccata accatgagtg ataacactgc    1680
ggccaactta cttctgacaa cgatcggagg accgaaggag ctaaccgctt ttttgcacaa    1740
catgggggat catgtaactc gccttgatcg ttgggaaccg gagctgaatg aagccatacc    1800
aaacgacgag cgtgacacca cgatgcctgt agcaatggca acaacgttgc gcaaactatt    1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg ggtctcgcgg tatcattgca gcactggggc cagatggtaa    2040
gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatcctttttt ttctgcgcgt    2340 aatctgctgc ttgcaaacaa aaaaaccacc gctaccagcg gtggtttgtt tgccggatca    2400
agagctacca actctttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880 gtcaggggg cggagcctat ggaaaaacgc cagcaacgcg ccttttttac ggttcctggc    2940
cttttgctgg ccttttgctc acatgttctt tcctgcgtta tcccctgatt ctgtggataa    3000
ccgtattacc gcctttgagt gagctgatac cgctcgccgc agccgaacga ccgagcgcag    3060
cgagtcagtg agcgaggaag cggaagagcg cctgatgcgg tatttttctcc ttacgcatct    3120 gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
```

```
caagctgtga ccgtctccgg gagctgcatg tgtcagaggt tttcaccgtc atcaccgaaa    3360
cgcgcgaggc agctgcggta aagctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag gcggttttt tcctgtttgg tcacttgatg cctccgtgta    3540 aggggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
tagcgaggtg ccgccggctt ccattcaggt cgaggtggcc cggctccatg caccgcgacg    4200
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg aagcgagaa gaatcataat    4440 ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
gaaggcttga gcgagggcgt gcaagattcc gaataccgca agcgacaggc cgatcatcgt    4620
cgcgctccag cgaaagcggt cctcgccgaa aatgacccag agcgctgccg gcacctgtcc    4680
tacgagttgc atgataaaga agacagtcat aagtgcggcg acgatagtca tgccccgcgc    4740
ccaccggaag gagctgactg ggttgaaggc tctcaagggc atcggtcgac caaactaaag    4800
cgcccttgtg gcgctttagt tttgttcatc ttccagcaag cgtgcgccgg taccttcttc    4860
tcctaagcgg tcgcccgggt tacgcaacgg gcaatcactg cgcgaaaggc agccacaacc    4920
aatacatccg tccagttcgt cacgcagcgc cactaaggta tgaatgcgcc gatccaactc    4980
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaacccctt tactttcata gaaatgcagc gccgataccg ccacaccgct    5220
gcgtttcgcc acttcgccgg gggttagcag cgctttaatg cggggtaatt tctttttccat    5280 aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
cttcggctac ggcctgcagt gcttcgcccg ctaccccgac cacatgaagc agcacgactt    5700
```

-continued

```
cttcaagtcc gccatgcccg aaggctacgt ccaggagcgc accatcttct tcaaggacga   5760
cggcaactac aagacccgcg ccgaggtgaa gttcgagggc gacaccctgg tgaaccgcat   5820
cgagctgaag ggcatcaact tcaaggagga cggcaacatc ctggggcaca agctggagta   5880
caactacaac agccacaacg tctatatcat ggccgacaag cagaagaacg gcatcaaggt   5940
gaacttcaag atccgccaca acatcgaggg cggcagcgtg cagctcgccg accactacca   6000
gcagaacacc cccatcggcg acggccccgt gctgctgccc gacaaccact acctgagcta   6060
ccagtccgcc ctgagcaaag accccaacga gaagcgcgat cacatggtcc tgctggagtt   6120
cgtgaccgcc gccgggatca ctctcggcat ggacgagctg tacaagtaat aaatcgatcc   6180
ggagcttatc gactgcacgg tgcaccaatg cttctggcgt caggcagcca tcggaagctg   6240
tggtatggct gtgcaggtcg taaatcactg cataattcgt gtcgctcaag gcgcactccc   6300
gttctggata atgttttttg cgccgacatc ataacggttc tggcaaatat tctgaaatga   6360
gctgttgaca attaatcatc ggctcgtata atgtgtggaa ttgtgagcgg ataacaattt   6420
cacacaggaa acagaa                                                    6436

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
acaagaattc gctaagagtg tcggcactcc                                       30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
ggccaagctt ccgaagaaga caccatcaag                                       30

<210> SEQ ID NO 20
<211> LENGTH: 6436
<212> TYPE: DNA
<213> ORGANISM: Artificial Sequence
<220> FEATURE:
<223> OTHER INFORMATION: vector

<400> SEQUENCE: 20
ttcatgtcta accgtttgga tggtaaggta gcaatcatta caggtggtac gttgggtatc     60
ggtttagcta tcgccacgaa gttcgttgaa gaaggggcta aggtcatgat taccggccgg    120
cacagcgatt tggtgaaaaa agcagctaag agtgtcggca ctcctgatca gattcaattt    180
ttccaacatg attcttccga tgaagacggc tggacgaaat tattcgatgc aacggaaaaa    240
gcctttggcc cagtttctac attagttaat aacgctggga tcatggttaa caagagtgtc    300
gaagaaacca cgactgctga atggcgtaaa ttattagccg tcaaccttga tggtgtcttc    360
ttcggtaccc gattagggat tcaacggatg aagaacaaag gcttaggggc ttccatcatc    420
aacatgtctt cgatcgaagg ctttgtgggt gatcctagct tagggcttta caacgcatct    480 aaggggccg tacggattat gtccaagtca gctgccttag attgtgccct aaaggactac    540
```

```
gatgttcggg taaacactgt tcaccctggc tacatcaaga caccattggt tgatgaccta      600
ccaggggccg aagaagcgat gtcacaacgg accaagacgc caatgggcca tatcggtgaa      660
cctaacgata ttgcctacat ctgtgtttac ttggcttcta acgaatctaa atttgcaacg      720
ggttctgaat ttgtagttga cggtggctac actgctcaat agtaagcttc tgttttggcg      780
gatgagagaa gattttcagc ctgatacaga ttaaatcaga acgcagaagc ggtctgataa      840
aacagaattt gcctggcggc agtagcgcgg tggtcccacc tgaccccatg ccgaactcag      900
aagtgaaacg ccgtagcgcc gatggtagtg tggggtctcc ccatgcgaga gtagggaact      960
gccaggcatc aaataaaacg aaaggctcag tcgaaagact gggccttttcg ttttatctgt     1020
tgtttgtcgg tgaacgctct cctgagtagg acaaatccgc cgggagcgga tttgaacgtt     1080
gcgaagcaac ggcccggagg gtggcgggca ggacgcccgc cataaactgc caggcatcaa     1140
attaagcaga aggccatcct gacggatggc cttttttgcgt ttctacaaac tcttttgttt    1200
attttttctaa atacattcaa atatgtatcc gctcatgaga caataaccct gataaatgct    1260
tcaataatat tgaaaaagga gagtatgag tattcaacat ttccgtgtcg cccttattcc      1320
ctttttttgcg gcattttgcc ttcctgtttt tgctcaccca gaaacgctgg tgaaagtaaa    1380
agatgctgaa gatcagttgg gtgcacgagt gggttacatc gaactggatc tcaacagcgg    1440
taagatcctt gagagttttc gccccgaaga acgttttcca atgatgagca cttttaaagt    1500
tctgctatgt ggcgcggtat tatcccgtgt tgacgccggg caagagcaac tcggtcgccg    1560
catacactat tctcagaatg acttggttga gtactcacca gtcacagaaa agcatcttac    1620
ggatggcatg acagtaagag aattatgcag tgctgccata accatgagtg ataacactgc    1680
ggccaactta cttctgacaa cgatcggagg accgaaggag ctaaccgctt ttttgcacaa    1740
catgggggat catgtaactc gccttgatcg ttgggaaccg gagctgaatg aagccatacc    1800
aaacgacgag cgtgacacca cgatgcctgt agcaatggca acaacgttgc gcaaactatt    1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg gtctcgcgg tatcattgca gcactggggc cagatggtaa    2040
gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatcctttttt ttctgcgcgt    2340
aatctgctgc ttgcaaacaa aaaaaccacc gctaccagcg gtggtttgtt tgccggatca    2400
agagctacca actctttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880
gtcaggggg cggagcctat ggaaaaacgc cagcaacgcg gcctttttac ggttcctggc    2940
```

```
cttttgctgg cctttttgctc acatgttctt tcctgcgtta tccctgatt ctgtggataa   3000
ccgtattacc gcctttgagt gagctgatac cgctcgccgc agccgaacga ccagcgcag   3060
cgagtcagtg agcgaggaag cggaagagcg cctgatgcgg tattttctcc ttacgcatct   3120
gtgcggtatt tcacaccgca tatggtgcac tctcagtaca atctgctctg atgccgcata   3180
gttaagccag tatacactcc gctatcgcta cgtgactggg tcatggctgc gccccgacac   3240
ccgccaacac ccgctgacgc gccctgacgg gcttgtctgc tcccggcatc cgcttacaga   3300
caagctgtga ccgtctccgg gagctgcatg tgtcagaggt tttcaccgtc atcaccgaaa   3360
cgcgcgaggc agctgcggta agctcatca gcgtggtcgt gaagcgattc acagatgtct   3420
gcctgttcat ccgcgtccag ctcgttgagt ttctccagaa gcgttaatgt ctggcttctg   3480
ataaagcggg ccatgttaag gcggttttt cctgtttgg tcacttgatg cctccgtgta   3540
aggggaatt tctgttcatg ggggtaatga taccgatgaa acgagagagg atgctcacga   3600
tacgggttac tgatgatgaa catgcccggt tactggaacg ttgtgagggt aaacaactgg   3660
cggtatggat gcggcgggac cagagaaaaa tcactcaggg tcaatgccag cgcttcgtta   3720
atacagatgt aggtgttcca cagggtagcc agcagcatcc tgcgatgcag atccggaaca   3780
taatggtgca gggcgctgac ttccgcgttt ccagacttta cgaaacacgg aaaccgaaga   3840
ccattcatgt tgttgctcag gtcgcagacg ttttgcagca gcagtcgctt cacgttcgct   3900
cgcgtatcgg tgattcattc tgctaaccag taaggcaacc ccgccagcct agccgggtcc   3960
tcaacgacag gagcacgatc atgcgcaccc gtggccagga cccaacgctg cccgagatgc   4020
gccgcgtgcg gctgctggag atggcggacg cgatggatat gttctgccaa gggttggttt   4080
gcgcattcac agttctccgc aagaattgat tggctccaat tcttggagtg gtgaatccgt   4140
tagcgaggtg ccgccggctt ccattcaggt cgaggtggcc cggctccatg caccgcgacg   4200
caacgcgggg aggcagacaa ggtatagggc ggcgcctaca atccatgcca acccgttcca   4260
tgtgctcgcc gaggcggcat aaatcgccgt gacgatcagc ggtccagtga tcgaagttag   4320
gctggtaaga gccgcgagcg atccttgaag ctgtccctga tggtcgtcat ctacctgcct   4380
ggacagcatg gcctgcaacg cgggcatccc gatgccgccg gaagcgagaa gaatcataat   4440
ggggaaggcc atccagcctc gcgtcgcgaa cgccagcaag acgtagccca gcgcgtcggc   4500
cgccatgccg gcgataatgg cctgcttctc gccgaaacgt tggtggcgg gaccagtgac   4560
gaaggcttga gcgagggcgt gcaagattcc gaataccgca agcgacaggc cgatcatcgt   4620
cgcgctccag cgaaagcggt cctcgccgaa aatgacccag agcgctgccg gcacctgtcc   4680
tacgagttgc atgataaaga agacagtcat aagtgcggcg acgatagtca tgccccgcgc   4740
ccaccggaag gagctgactg ggttgaaggc tctcaagggc atcggtcgac caaactaaag   4800
cgcccttgtg gcgctttagt tttgttcatc ttccagcaag cgtgcgccgg taccttcttc   4860
tcctaagcgt tcgcccgggt tacgcaacgg gcaatcactg cgcgaaaggc agccacaacc   4920
aatacatccg tccagttcgt cacgcagcgc cactaaggta tgaatgcgcc gatccaactc   4980
ttctcgccat tgggacgaaa gctgttttcca ctctttcgca cttaacgtat gcccttcggg   5040
caacacgcca aacgcttcac caatggtcgc cagcggaatg ccaatacgct gagcaatttt   5100
gataattgca acatatcgca acacatcacg tttatatcgc cgctgattgc cgctgttacg   5160
gatactggta atcaaccctt tactttcata gaaatgcagc gccgataccg ccacaccgct   5220
gcgtttcgcc acttcgccgg gggttagcag cgctttaatg cggggtaatt tcttttccat   5280
```

```
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
cttcggctac ggcctgcagt gcttcgcccg ctaccccgac cacatgaagc agcacgactt    5700
cttcaagtcc gccatgcccg aaggctacgt ccaggagcgc accatcttct caaggacga    5760 cggcaactac aagacccgcg ccgaggtgaa gttcgagggc gacaccctgg tgaaccgcat    5820
cgagctgaag ggcatcaact tcaaggagga cggcaacatc ctggggcaca gctggagta    5880 caactacaac agccacaacg tctatatcat ggccgacaag cagaagaacg gcatcaaggt    5940
gaacttcaag atccgccaca acatcgaggg cggcagcgtg cagctcgccg accactacca    6000
gcagaacacc cccatcggcg acggccccgt gctgctgccc gacaaccact acctgagcta    6060
ccagtccgcc ctgagcaaag accccaacga gaagcgcgat cacatggtcc tgctggagtt    6120
cgtgaccgcc gccgggatca ctctcggcat ggacgagctg tacaagtaat aaatcgatcc    6180
ggagcttatc gactgcacgg tgcaccaatg cttctggcgt caggcagcca tcggaagctg    6240
tggtatggct gtgcaggtcg taaatcactg cataattcgt gtcgctcaag cgcactccc    6300 gttctggata atgtttttg cgccgacatc ataacggttc tggcaaatat tctgaaatga    6360
gctgttgaca attaatcatc ggctcgtata atgtgtggaa ttgtgagcgg ataacaattt    6420
cacacaggaa acagaa                                                   6436
```

<210> SEQ ID NO 21
<211> LENGTH: 31
<212> TYPE: DNA
<213> ORGANISM: Artificial Sequence
<220> FEATURE:
<223> OTHER INFORMATION: SoxS_for_SphI_t1

<400> SEQUENCE: 21
atctgcatgc cggctggtca atatgctcgt c                                  31

<210> SEQ ID NO 22
<211> LENGTH: 30
<212> TYPE: DNA
<213> ORGANISM: Artificial Sequence
<220> FEATURE:
<223> OTHER INFORMATION: SoxR_rev_SalI_t1

<400> SEQUENCE: 22
gctagtcgac caaactaaag cgcccttgtg                                    30

<210> SEQ ID NO 23
<211> LENGTH: 26
<212> TYPE: DNA
<213> ORGANISM: Artificial Sequence
<220> FEATURE:
<223> OTHER INFORMATION: EYFP_for_SphI_t1

<400> SEQUENCE: 23
agaggcatgc gtgagcaagg gcgagg                                        26

<210> SEQ ID NO 24
<211> LENGTH: 35

```
<212> TYPE: DNA
<213> ORGANISM: Artificial Sequence
<220> FEATURE:
<223> OTHER INFORMATION: EYFP_rev_ClaI_tl

<400> SEQUENCE: 24
gcgcatcgat ttattacttg tacagctcgt ccatg                               35

<210> SEQ ID NO 25
<211> LENGTH: 6418
<212> TYPE: DNA
<213> ORGANISM: Artificial Sequence
<220> FEATURE:
<223> OTHER INFORMATION: pSenSox_tl

<400> SEQUENCE: 25
ttcatgtcta accgtttgga tggtaaggta gcaatcatta caggtggtac gttgggtatc    60
ggtttagcta tcgccacgaa gttcgttgaa aaggggctaa aggtcatgat taccggccgg   120
cacagcgatt ttggtgaaaa agcagctaag agtgtcggca ctcctgatca gattcaattt   180
ttccaacatg attcttccga tgaagacggc tggacgaaat tattcgatgc aacggaaaaa   240
gcctttggcc cagtttctac attagttaat aacgctggga tcgcggttaa caagagtgtc   300
gaagaaacca cgactgctga atggcgtaaa ttattagccg tcaaccttga tggtgtcttc   360
ttcggtaccc gattagggat tcaacggatg aagaacaaag cttagggggc ttccatcatc   420
aacatgtctt cgatcgaagg cttttgtgggt gatcctagct tagggcttaa caacgcatct   480
aaaggggccg tacggattat gtccaagtca gctgccttag attgtgccct aaaggactac   540
gatgttcggg taaacactgt tcaccctggc tacatcaaga caccattggt tgatgaccta   600
ccaggggccg aagaagcgat gtcacaacgg accaagacgc caatgggcca tatcggtgaa   660
cctaacgata ttgcctacat ctgtgtttac ttggcttcta acgaatctaa atttgcaacg   720
ggttctgaat ttgtagttga cggtggctac actgctcaat agtaagcttc tgttttggcg   780
gatgagagaa gattttcagc ctgatacaga ttaaatcaga acgcagaagc ggtctgataa   840
aacagaattt gcctggcggc agtagcgcgg tggtcccacc tgaccccatg ccgaactcag   900
aagtgaaacg ccgtagcgcc gatggtagtg tggggtctcc ccatgcgaga gtagggaact   960
gccaggcatc aaataaaacg aaaggctcag tcgaaagact gggcctttcg ttttatctgt  1020
tgtttgtcgg tgaacgctct cctgagtagg acaaatccgc cgggagcgga tttgaacgtt  1080
gcgaagcaac ggcccggagg gtggcgggca ggacgcccgc cataaactgc caggcatcaa  1140
attaagcaga aggccatcct gacgatggcc ttttttgcgt ttctacaaac tctttttgttt  1200 attttctaa atacattcaa atatgtatcc gctcatgaga caataaccct gataaatgct  1260 tcaataaatat tgaaaaagga agagtatgag tattcaacat ttccgtgtcg cccttattcc  1320
cttttttgcg gcattttgcc ttcctgtttt tgctcaccca gaaacgctgg tgaaagtaaa  1380
agatgctgaa gatcagttgg gtgcacgagt gggttacatc gaactggatc tcaacagcgg  1440
taagatcctt gagagttttc gccccgaaga acgttttcca atgatgagca cttttaaagt  1500
tctgctatgt ggcgcggtat tatcccgtgt tgacgccggg caagagcaac tcggtcgccg  1560
catacactat tctcagaatg acttggttga gtactcacca gtcacagaaa agcatcttac  1620
ggatggcatg acagtaagag aattatgcag tgctgccata accatgagtg ataacactgc  1680
ggccaactta cttctgacaa cgatcggagg accgaaggag ctaaccgctt ttttgcacaa  1740
catgggggat catgtaactc gccttgatcg ttgggaaccg gagctgaatg aagccatacc  1800
```

```
aaacgacgag cgtgacacca cgatgcctgt agcaatggca caacgttgc gcaaactatt    1860 aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg ggtctcgcgg tatcattgca gcactgggc cagatggtaa     2040 gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa atcccttaa cgtgagtttt cgttccactg     2280
agcgtcagac cccgtagaaa agatcaaagg atcttcttga tccttttt ttctgcgcgt      2340 aatctgctgc ttgcaaacaa aaaaaccacc gctaccagcg gtggtttgtt tgccggatca    2400
agagctacca actctttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccaggggaa acgcctggta     2820 tctttatagt cctgtcgggt ttcgccacct ctgacttgag cgtcgatttt tgtgatgctc    2880 gtcaggggg cggagcctat ggaaaaacgc cagcaacgcg gcctttttac ggttcctggc     2940
cttttgctgg ccttttgctc acatgttctt tcctgcgtta tcccctgatt ctgtggataa    3000
ccgtattacc gcctttgagt gagctgatac cgctcgccgc agccgaacga ccgagcgcag    3060
cgagtcagtg agcgaggaag cggaagagcg cctgatgcgg tattttctcc ttacgcatct    3120
gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
caagctgtga ccgtctccgg gagctgcatg tgtcagaggt tttcaccgtc atcaccgaaa    3360
cgcgcgaggc agctgcggta agctcatca gcgtggtcgt gaagcgattc acagatgtct     3420
gcctgttcat ccgcgtccag ctcgttgagt ttctccagaa gcgttaatgt ctggcttctg    3480
ataaagcggg ccatgttaag gcggttttt tcctgtttgg tcacttgatg cctccgtgta    3540
agggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
tagcgaggtg ccgccggctt ccattcaggt cgaggtggcc cggctccatg caccgcgacg    4200
```

```
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg gaagcgagaa gaatcataat    4440
ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
gaaggcttga gcgagggcgt gcaagattcc gaataccgca agcgacaggc cgatcatcgt    4620
cgcgctccag cgaaagcggt cctcgccgaa aatgacccag agcgctgccg gcacctgtcc    4680
tacgagttgc atgataaaga agacagtcat aagtgcggcg acgatagtca tgccccgcgc    4740
ccaccggaag gagctgactg ggttgaaggc tctcaagggc atcggtcgac caaactaaag    4800
cgccttgtg gcgctttagt tttgttcatc ttccagcaag cgtgcgccgg taccttcttc    4860
tcctaagcgg tcgcccgggt tacgcaacgg gcaatcactg cgcgaaaggc agccacaacc    4920
aatacatccg tccagttcgt cacgcagcgc cactaaggta tgaatgcgcc gatccaactc    4980
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaacccctt tactttcata gaaatgcagc gccgataccg ccacaccgct    5220
gcgtttcgcc acttcgccgg gggttagcag cgctttaatg cggggtaatt tcttttccat    5280
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccggc atgcgtgagc aagggcgagg agctgttcac    5460
cggggtggtg cccatcctgg tcgagctgga cggcgacgta aacggccaca gttcagcgt    5520
gtccggcgag ggcgagggcg atgccaccta cggcaagctg accctgaagt tcatctgcac    5580
caccggcaag ctgcccgtgc cctggcccac cctcgtgacc accttcggct acggcctgca    5640
gtgcttcgcc cgctacccccg accacatgaa gcagcacgac ttcttcaagt ccgccatgcc    5700
cgaaggctac gtccaggagc gcaccatctt cttcaaggac gacggcaact acaagacccg    5760
cgccgaggtg aagttcgagg gcgacaccct ggtgaaccgc atcgagctga agggcatcaa    5820
cttcaaggag gacggcaaca tcctggggca caagctggag tacaactaca acagccacaa    5880
cgtctatatc atggccgaca agcagaagaa cggcatcaag gtgaacttca agatccgcca    5940
caacatcgag gcggcagcg tgcagctcgc cgaccactac cagcagaaca ccccccatcgg    6000
cgacggcccc gtgctgctgc ccgacaacca ctacctgagc taccagtccg ccctgagcaa    6060
agaccccaac gagaagcgcg atcacatggt cctgctggag ttcgtgaccg ccgccgggat    6120
cactctcggc atggacgagc tgtacaagta ataaatcgat ccggagctta tcgactgcac    6180
ggtgcaccaa tgcttctggc gtcaggcagc catcggaagc tgtggtatgg ctgtgcaggt    6240
cgtaaatcac tgcataattc gtgtcgctca aggcgcactc ccgttctgga taatgttttt    6300
tgcgccgaca tcataacggt tctggcaaat attctgaaat gagctgttga caattaatca    6360
tcggctcgta taatgtgtgg aattgtgagc ggataacaat ttcacacagg aaacagaa      6418
```